(12) United States Patent
Fujiwara

(10) Patent No.: US 12,115,051 B2
(45) Date of Patent: Oct. 15, 2024

(54) DISPOSABLE WEARABLE ARTICLE

(71) Applicant: Daio Paper Corporation, Ehime (JP)

(72) Inventor: Yuto Fujiwara, Ehime (JP)

(73) Assignee: Daio Paper Corporation, Ehime (JP)

( * ) Notice: Subject to any disclaimer, the term of this patent is extended or adjusted under 35 U.S.C. 154(b) by 361 days.

(21) Appl. No.: 17/772,885

(22) PCT Filed: Nov. 18, 2020

(86) PCT No.: PCT/JP2020/043054
§ 371 (c)(1),
(2) Date: Apr. 28, 2022

(87) PCT Pub. No.: WO2021/100775
PCT Pub. Date: May 27, 2021

(65) Prior Publication Data
US 2022/0370266 A1    Nov. 24, 2022

(30) Foreign Application Priority Data

Nov. 20, 2019  (JP) .................................. 2019-209780

(51) Int. Cl.
*A61F 13/512*      (2006.01)
*A61F 13/511*      (2006.01)
(Continued)

(52) U.S. Cl.
CPC .... *A61F 13/5126* (2013.01); *A61F 13/51121* (2013.01); *A61F 13/51456* (2013.01);
(Continued)

(58) Field of Classification Search
CPC ............ A61F 13/5126; A61F 13/51121; A61F 13/51456; A61F 2013/15406;
(Continued)

(56) References Cited

U.S. PATENT DOCUMENTS 4,834,735 A * 5/1989 Alemany .......... A61F 13/53752
                                                            428/218
4,988,344 A * 1/1991 Reising ................. A61F 13/535
                                                            604/378

(Continued)

FOREIGN PATENT DOCUMENTS

CN        110302013       10/2019
JP        2001-328191     11/2001
(Continued)

OTHER PUBLICATIONS

International Search Report for PCT/JP2020/043054, dated Jan. 26, 2021.

*Primary Examiner* — Guy K Townsend
(74) *Attorney, Agent, or Firm* — Andrus Intellectual Property Law, LLP

(57) ABSTRACT

A disposable wearable article has a top sheet constituting a surface for use, a liquid-impervious sheet provided on the under face side, and an absorbent element interposed therebetween, wherein the top sheet is formed of perforated nonwoven fabric having a number of holes arranged at intervals and each penetrating two sides of the fabric. The absorbent element includes an absorber body and a packing sheet covering the absorber body. The packing sheet is formed of laminated nonwoven fabric having a spunbonded layer and a melt-blown layer, and a moisturizer composed mainly of glycerin is applied to an exterior surface of the top sheet.

6 Claims, 16 Drawing Sheets

(51) Int. Cl.
*A61F 13/514* (2006.01)
*A61F 13/15* (2006.01)
*A61F 13/513* (2006.01)
*A61F 13/534* (2006.01)

(52) U.S. Cl.
CPC ............... *A61F 2013/15406* (2013.01); *A61F 2013/51117* (2013.01); *A61F 2013/51316* (2013.01); *A61F 2013/53472* (2013.01)

(58) Field of Classification Search
CPC .. A61F 2013/51316; A61F 2013/53472; F61F 2013/51117
See application file for complete search history.

(56) References Cited

U.S. PATENT DOCUMENTS

| | | | | |
|---|---|---|---|---|
| 6,153,209 A | * | 11/2000 | Vega | A61F 13/8405 604/382 |
| 6,726,386 B1 | * | 4/2004 | Gruenbacher | B65D 81/3266 401/133 |
| 12,016,756 B2 | * | 6/2024 | Newman | A61F 13/51108 |
| 2001/0029141 A1 | * | 10/2001 | Mizutani | A61F 13/513 428/131 |
| 2004/0102750 A1 | * | 5/2004 | Jameson | A61F 13/511 604/367 |
| 2006/0135932 A1 | * | 6/2006 | Abuto | A61F 13/531 604/368 |
| 2006/0173432 A1 | * | 8/2006 | Laumer | A61L 15/60 604/372 |
| 2006/0246272 A1 | * | 11/2006 | Zhang | A61F 13/53708 428/304.4 |
| 2007/0135785 A1 | * | 6/2007 | Qin | A61F 13/534 604/366 |
| 2007/0255243 A1 | * | 11/2007 | Kaun | A61F 13/534 604/385.101 |
| 2008/0054408 A1 | * | 3/2008 | Tippey | A61F 13/42 257/621 |
| 2008/0058747 A1 | * | 3/2008 | Singh Kainth | A61L 15/26 604/372 |
| 2008/0082068 A1 | * | 4/2008 | Qin | A61L 15/42 604/372 |
| 2008/0082069 A1 | * | 4/2008 | Qin | A61L 15/60 604/372 |
| 2008/0147026 A1 | * | 6/2008 | Qin | A61L 15/28 8/147 |
| 2008/0234645 A1 | * | 9/2008 | Dodge | A61L 15/60 604/368 |
| 2008/0269705 A1 | * | 10/2008 | Kainth | A61F 13/531 604/367 |
| 2009/0041820 A1 | * | 2/2009 | Wu | A61Q 13/00 252/194 |
| 2009/0155325 A1 | * | 6/2009 | Wenzel | A61F 13/8405 514/769 |
| 2011/0057346 A1 | * | 3/2011 | Nunn | D04H 1/4274 28/103 |
| 2012/0089067 A1 | * | 4/2012 | Zhou | A61L 15/46 604/360 |
| 2013/0066289 A1 | * | 3/2013 | Song | A61L 15/56 604/361 |
| 2013/0158492 A1 | * | 6/2013 | Song | A61L 15/56 436/39 |
| 2013/0240139 A1 | * | 9/2013 | Zhou | B32B 5/022 156/276 |
| 2017/0258650 A1 | * | 9/2017 | Rosati | D04H 1/42 |
| 2020/0375811 A1 | * | 12/2020 | Newman | A61F 13/15203 |

FOREIGN PATENT DOCUMENTS

| | | | | |
|---|---|---|---|---|
| JP | 2013-066598 | | 4/2013 | |
| JP | 2013-066598 A | * | 4/2013 | ........... A61F 13/512 |
| JP | 2015-128573 | | 7/2015 | |
| JP | 2018-102828 | | 7/2018 | |
| JP | 2019-171023 | | 10/2019 | |

* cited by examiner

[FIG.1]
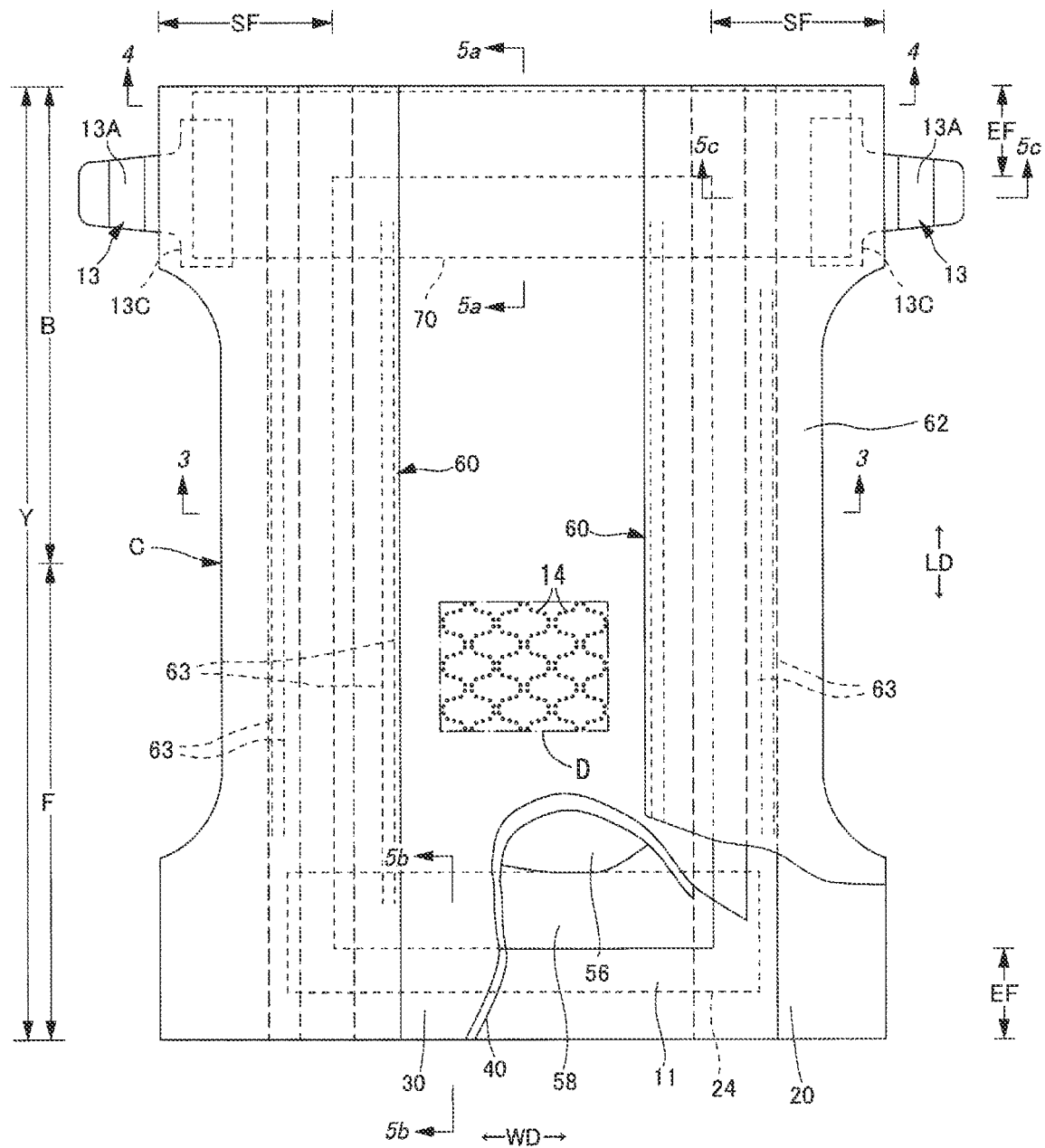

[FIG.2]
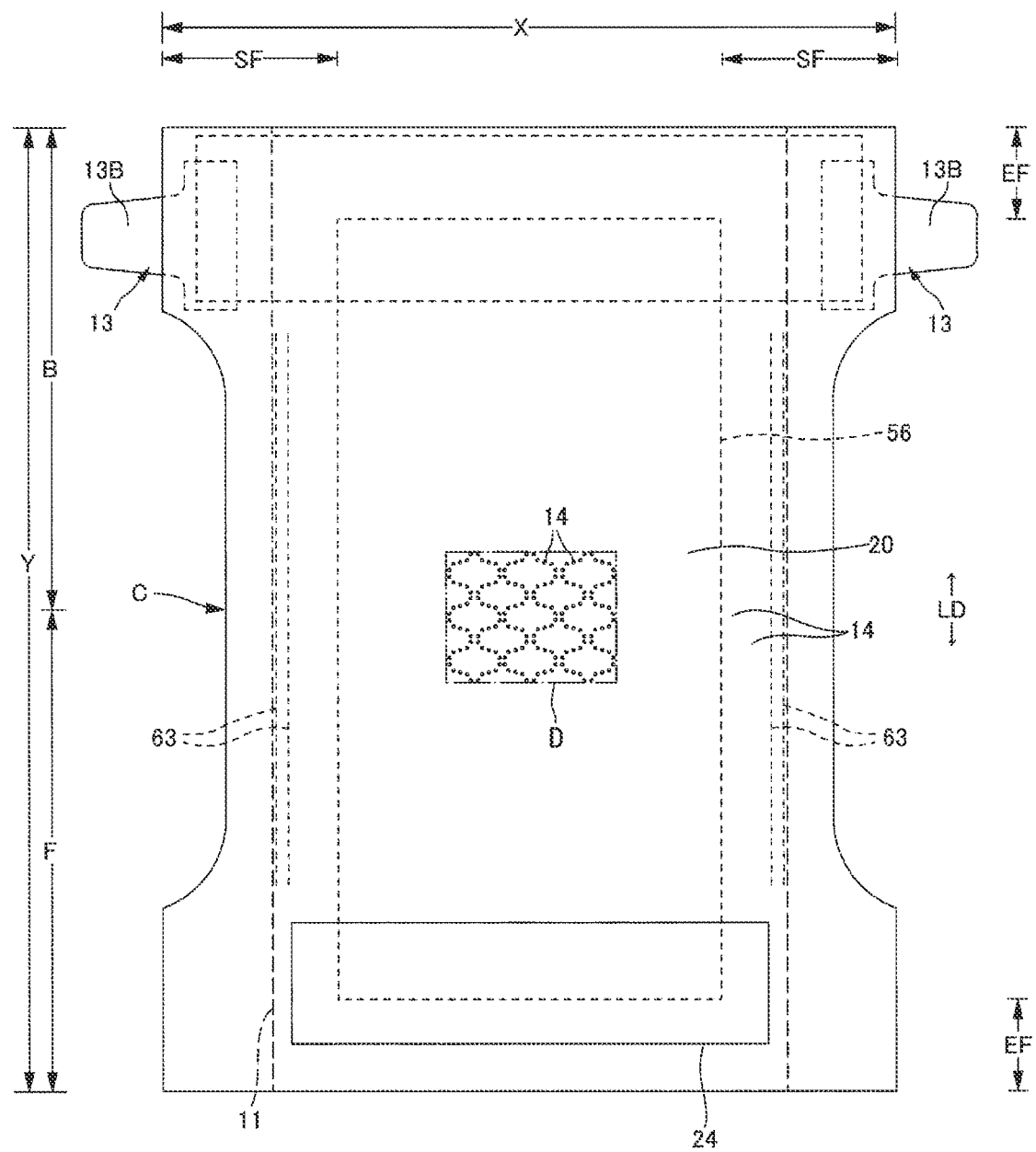

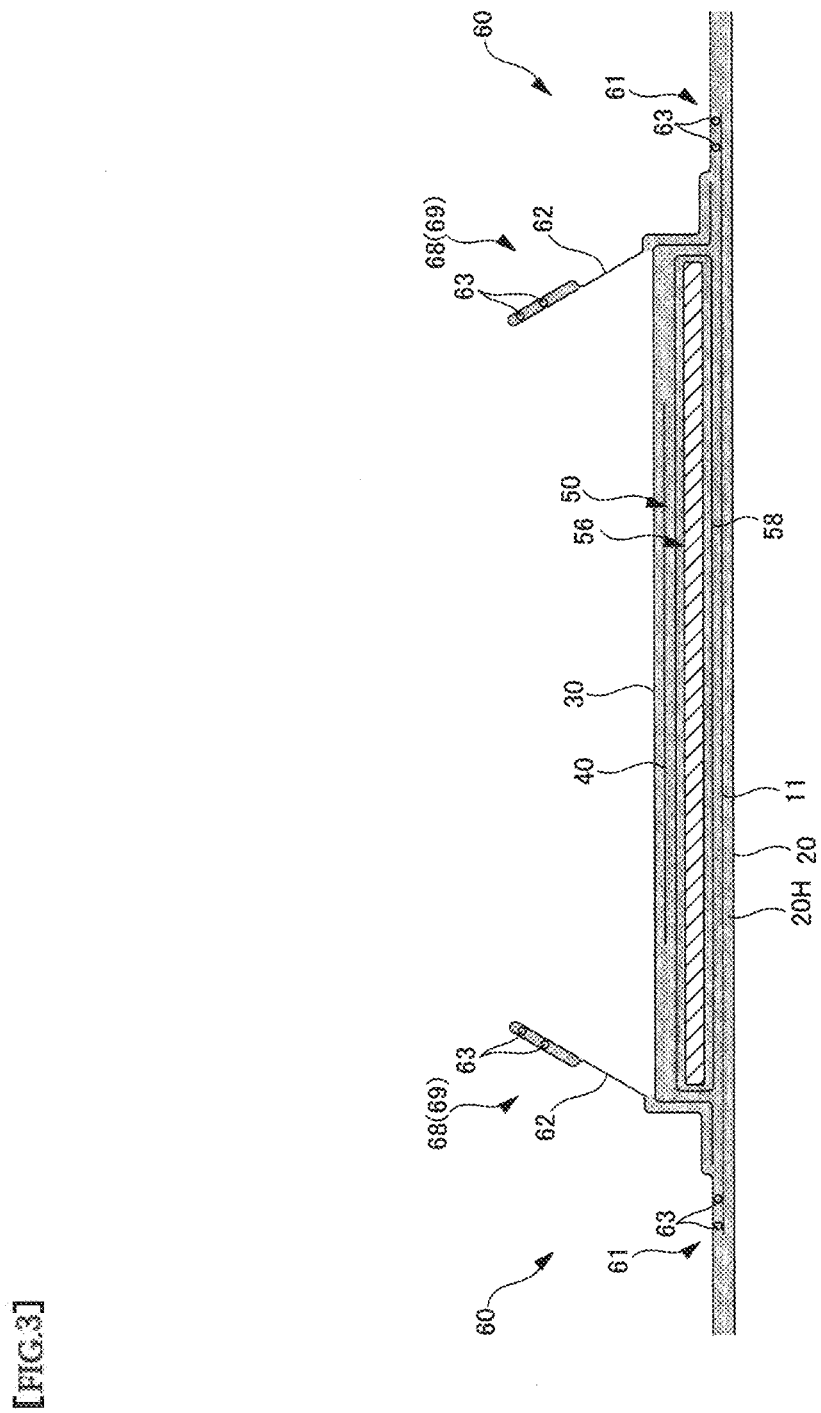
[FIG.3]

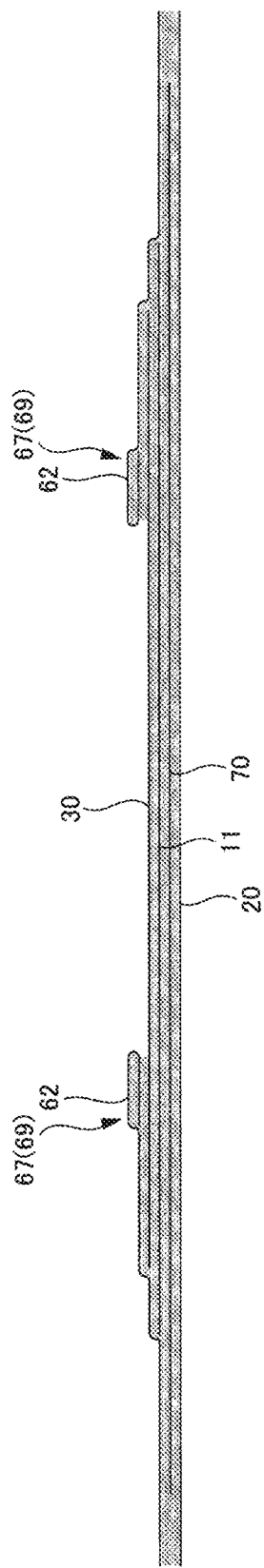

[FIG.5]
(a)
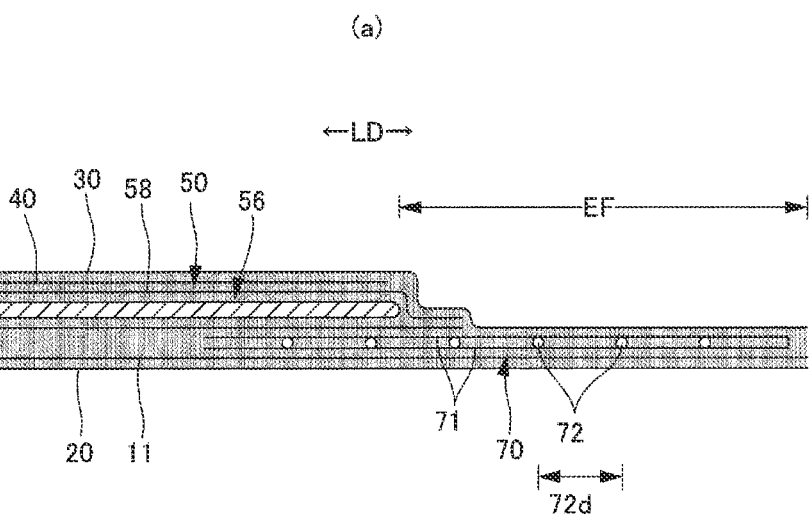
(b)
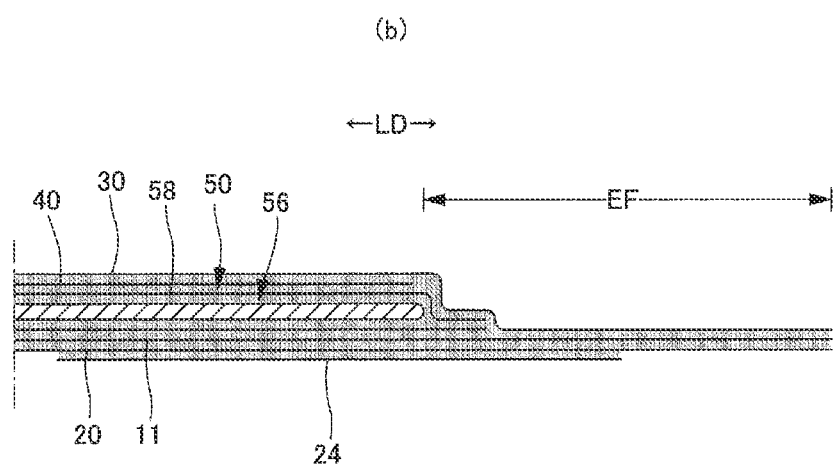
(c)
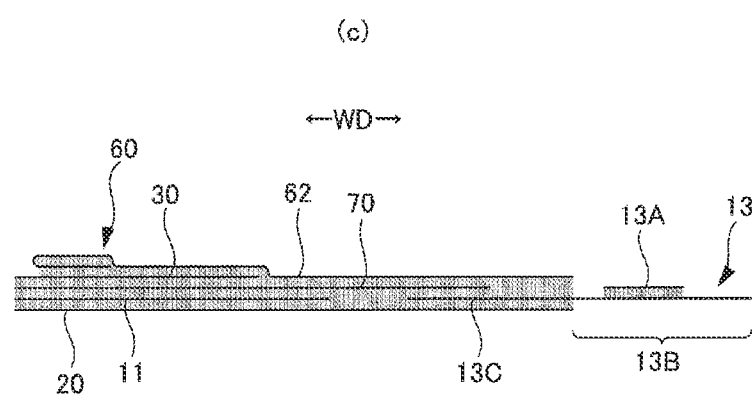

[FIG.6]
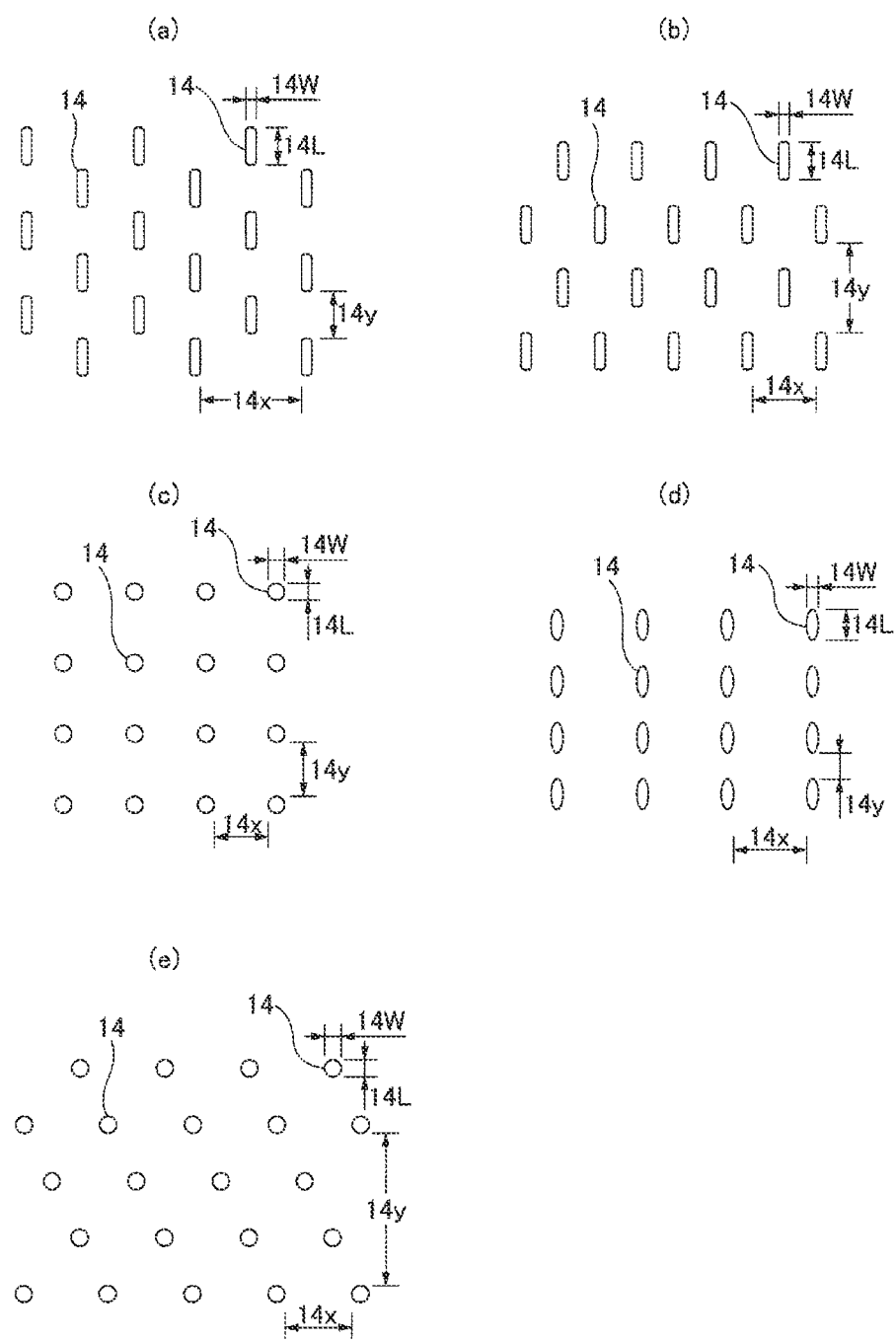

[FIG.7]
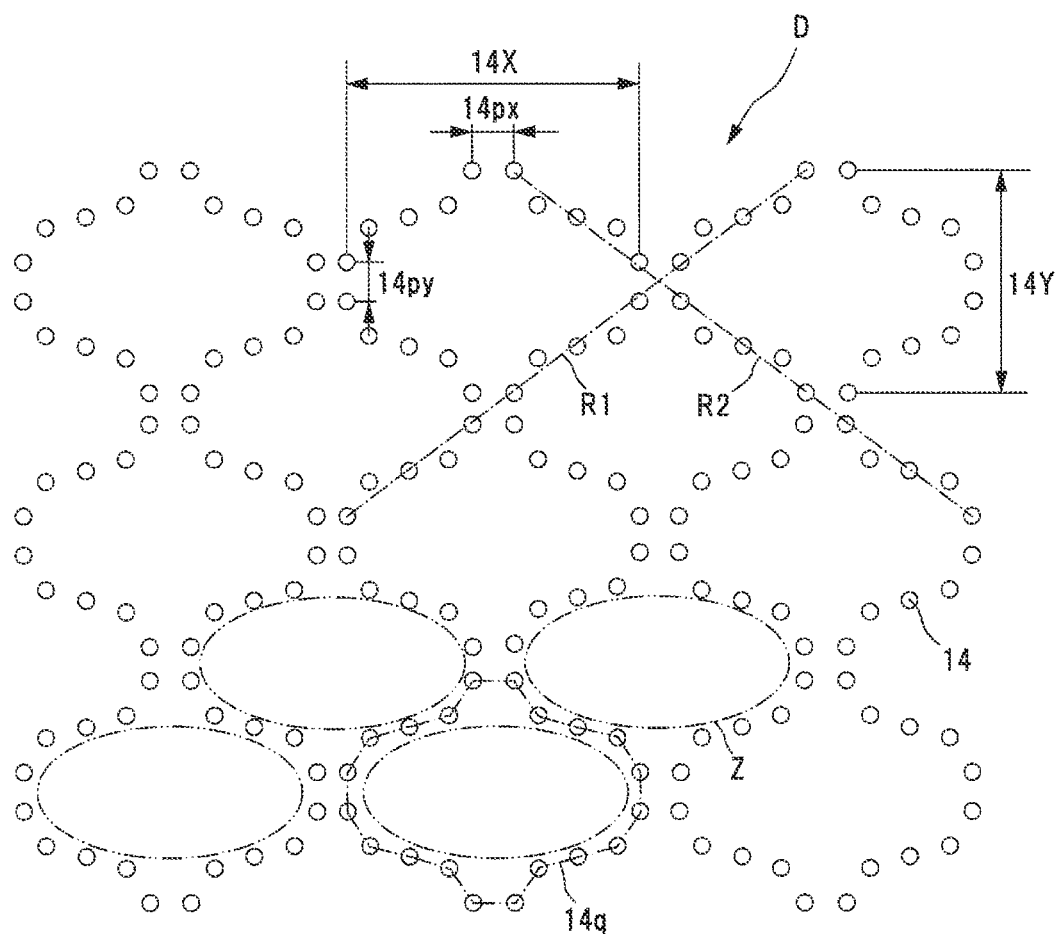

[FIG.8]
(a)
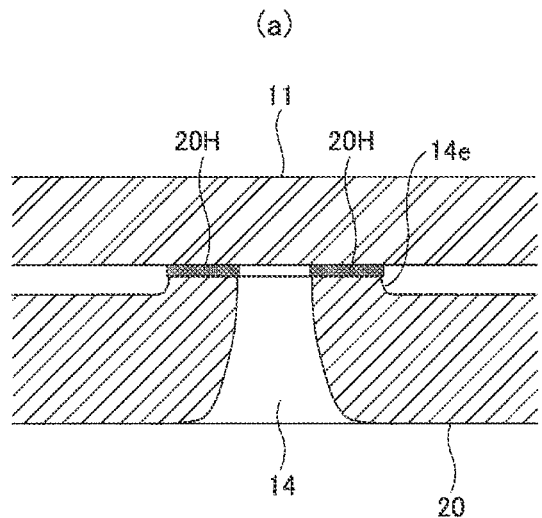
(b)
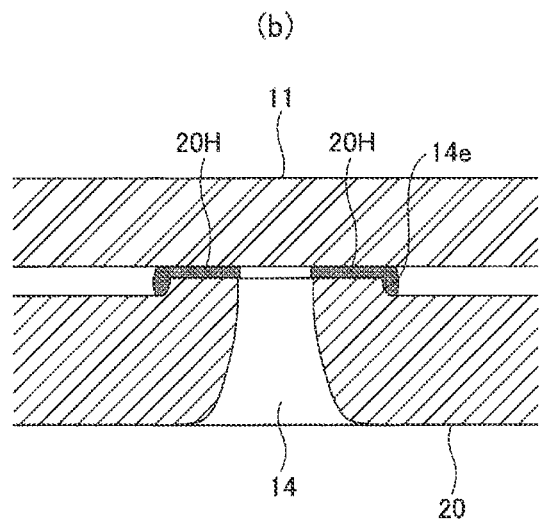
(c)
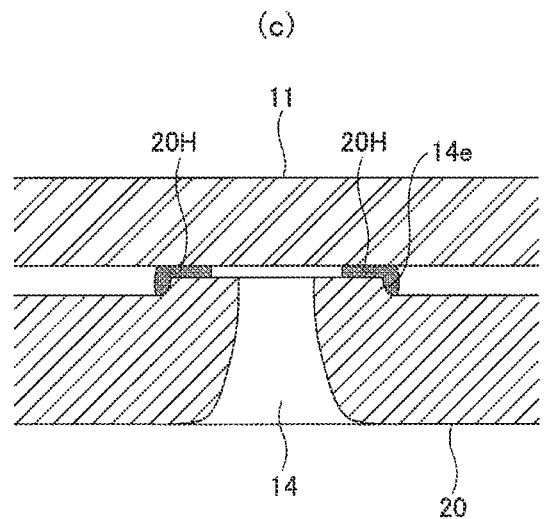

[FIG.9]
(a)
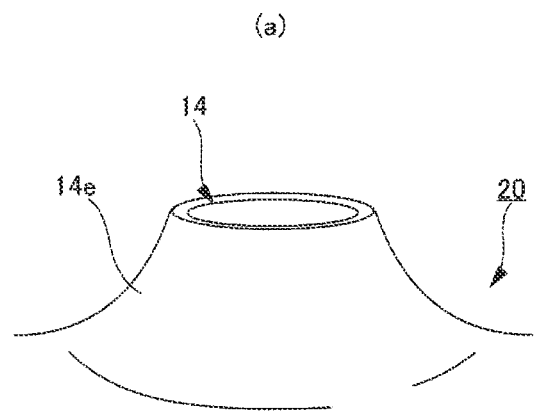
(b)
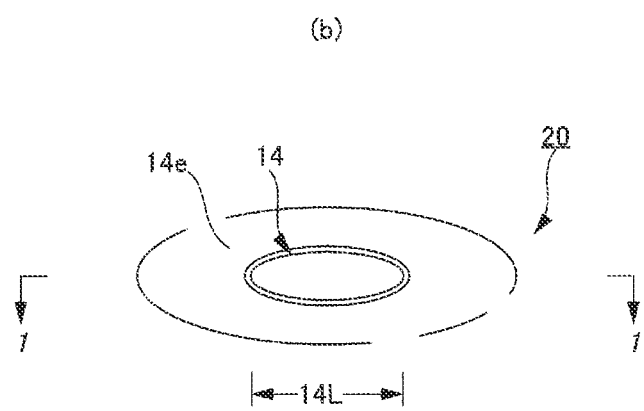
(c)
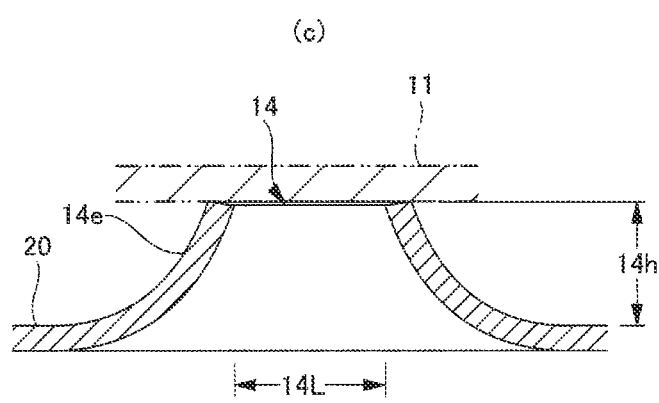

[FIG.10]
(a)
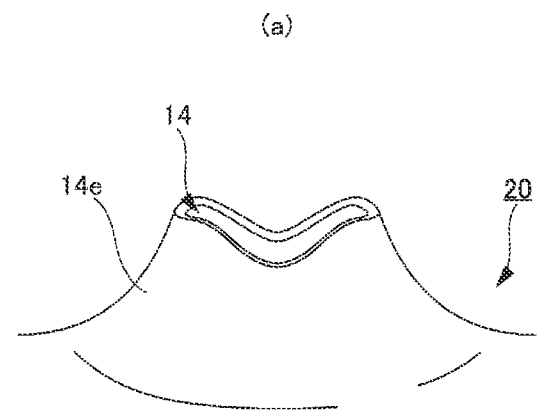
(b)
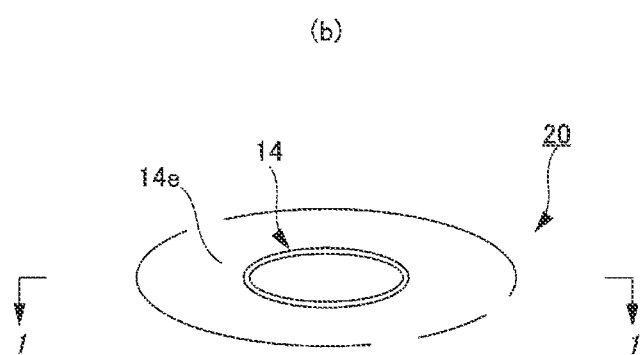
(c)
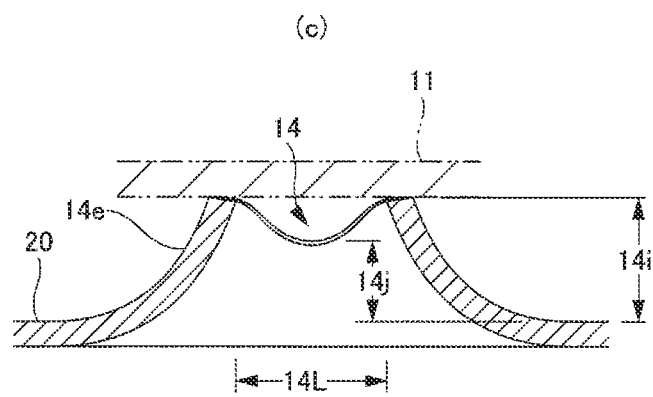

[FIG.11]
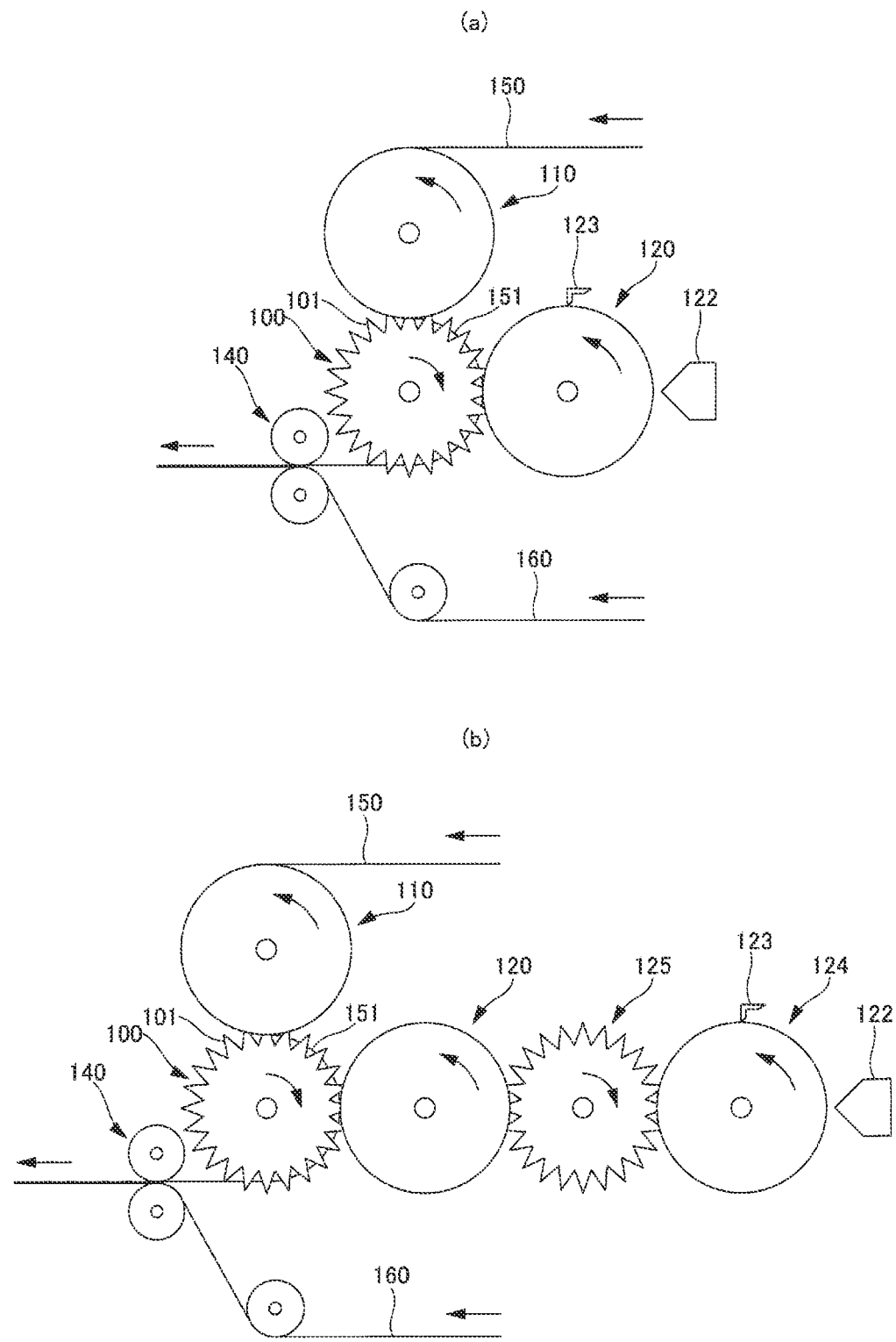

[FIG.12]
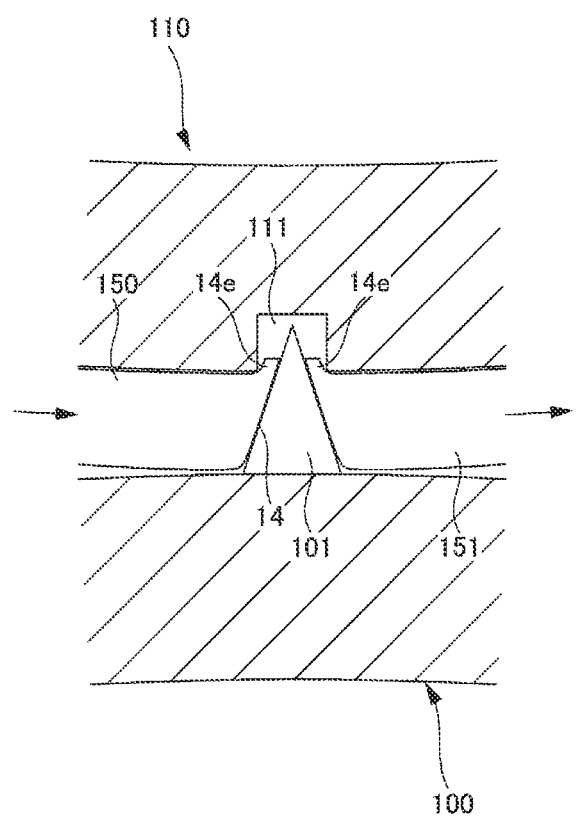

[FIG.13]
(a) 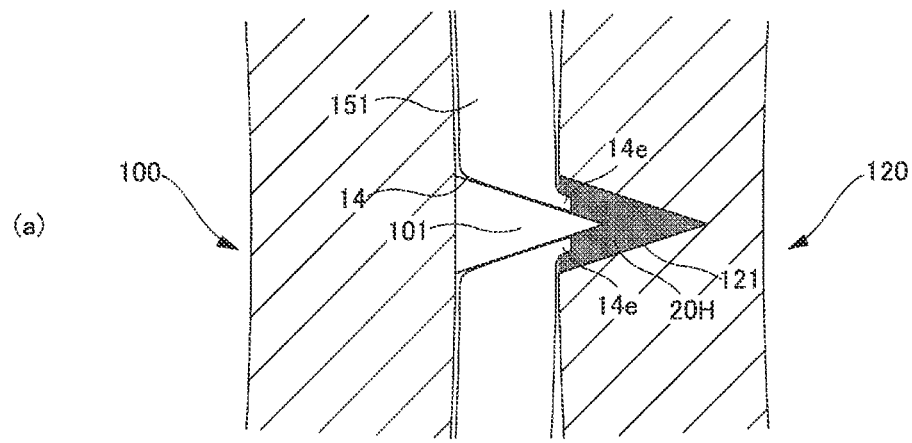
(b) 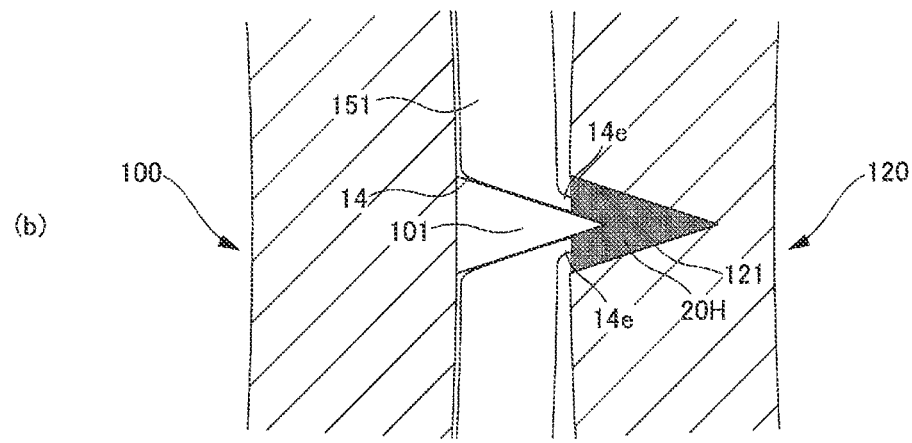
(c) 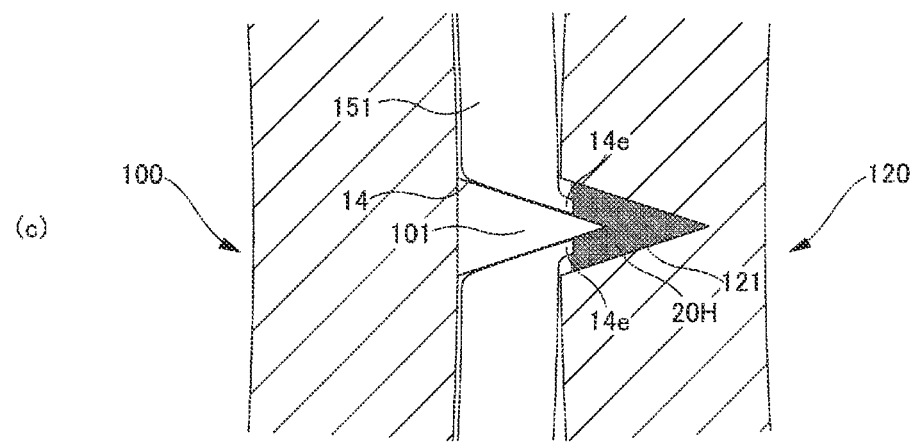

[FIG.14]
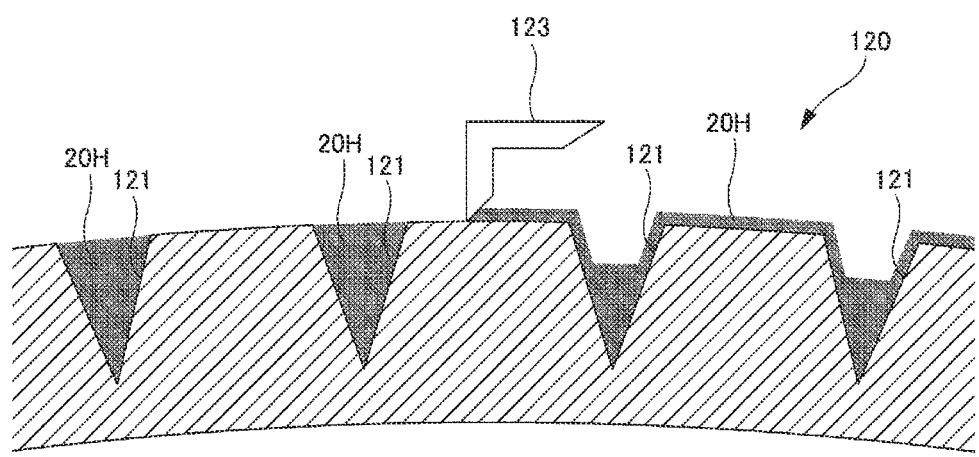

[FIG.15]
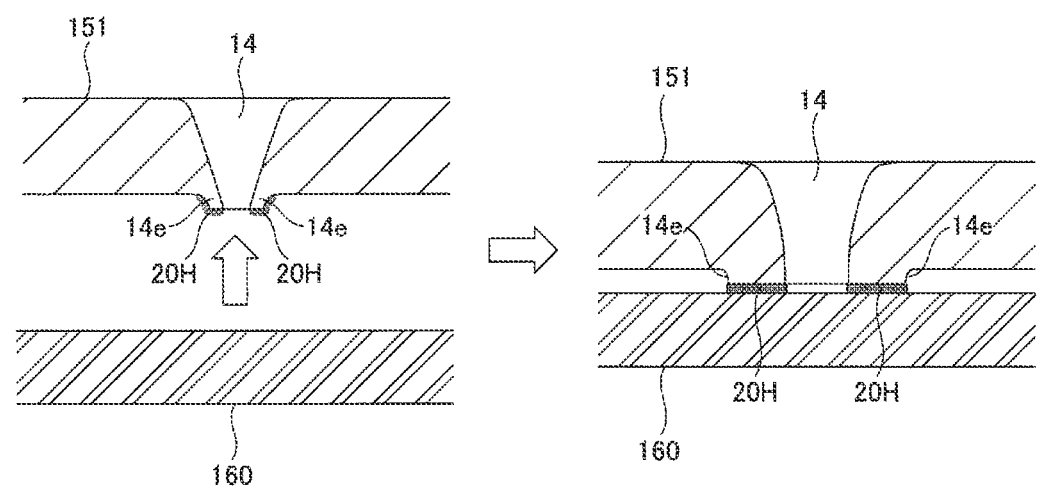

[FIG.16]
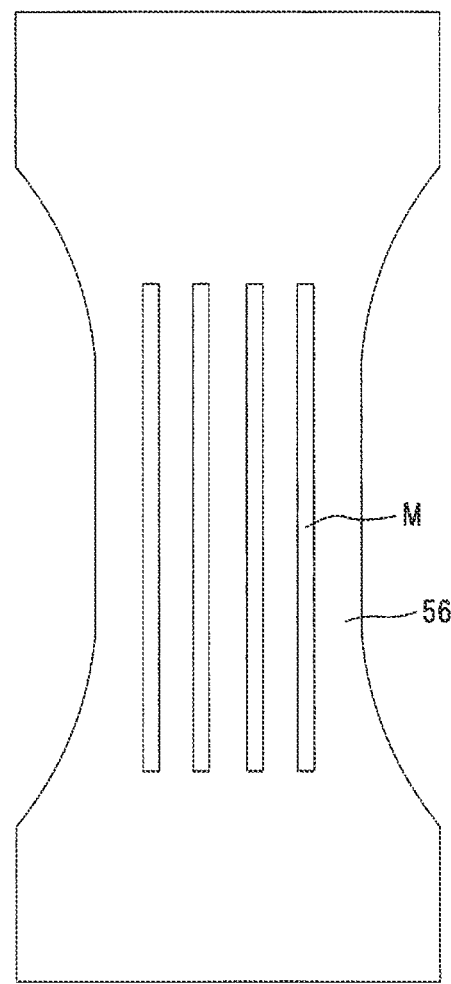

DISPOSABLE WEARABLE ARTICLE

CROSS-REFERENCE TO RELATED APPLICATIONS

This application is the U.S. national stage application of International Application PCT/JP2020/043054, filed Nov. 18, 2020, which international application was published on May 27, 2021, as International Publication WO 2021/100775 in the Japanese language. The International Application claims priority of Japanese Patent Application No. 2019-209780, filed Nov. 20, 2019. The international application and Japanese application are both incorporated herein by reference, in entirety.

TECHNICAL FIELD

The present invention relates to disposable wearable articles, such as disposable diapers or sanitary napkins.

BACKGROUND ART

Disposable wearable articles, particularly, disposable diapers, often pose skin problems, in particular, skin rash of wearers.

Such problems may result from friction between the skin and a diaper when worn, or irritation to the skin caused by body fluid or bodily waste (urine, loose stool) when a diaper is worn over a prolonged period of time.

In particular, irritation to the skin caused by loose stool being in contact with skin for a long period of time is a major factor. This may be avoided by diapers promptly absorbing loose stool into an absorber body. Diapers promptly absorbing loose stool into an absorber body may help not only in reducing skin irritation, but also in preventing leakage through leg portion or back portion of the diaper.

A major factor in obstructing absorption of loose stool through a top sheet is that components of loose stool that are incapable of permeating the top sheet remain on the surface of the fibers constituting the top sheet to cause clogging. A second major factor is that the defecation speed is faster than the absorption rate of diapers, resulting in unabsorbed loose stool components remaining on the top sheet.

The loose stool components remaining on the top sheet may slide on the top sheet to cause leakage of the loose stool.

Accordingly, it is of crucial importance to cause diapers to promptly absorb loose stool into the absorber.

Patent Literature 1 discloses to provide a skin care medicine between so-called gather cuffs of a diaper disposed on its widthwise opposite sides.

The skin care medicine is arranged on the top sheet, and may contain, for example, a diamide derivative as an active component.

On the other hand, it is a major task for disposable wearable articles to avoid leakage of body fluid. Leakage of body fluid may result from exceedance of the absorption limit of the absorber by body fluid, or posture change of a wearer.

Posture change of a wearer may cause bodily wastes to override the gather cuffs, or cause the diaper to be displaced with respect to the wearer to generate a gap between the diaper and the skin of the wearer, resulting in leakage of body fluid.

Means for keeping up with the posture change of a wearer may include formation of a longitudinal recess in the absorber to make it conform to the crotch (Patent Literature 2).

PRIOR ART LITERATURE

Patent Literature

Patent Literature 1: JP 2015-128573 A
Patent Literature 2: JP 2018-102828 A

SUMMARY OF THE INVENTION

Problems to be Solved by the Invention

The present inventor has found out that there is a limit on controlling skin problems with the skin care medicine containing a diamide derivative as an active component.

There is also a limit in the configuration as disclosed in Patent Literature 2 to avoid leakage of body fluid due to posture change of a wearer.

In view of the above, it is a primary object of the present invention to provide a disposable wearable article that protects the skin of a wearer and avoids leakage of body fluid caused by posture change of the wearer.

Means for Solving the Problem

Typical aspects of the present invention solving the above problems are as follows.
<Typical Aspect>
A disposable wearable article including a top sheet constituting a surface for use, a liquid-impervious sheet provided on an under face side, and an absorbent element interposed therebetween,
wherein the top sheet is formed of perforated nonwoven fabric having a number of holes arranged at intervals and each penetrating two sides of the fabric,
wherein the absorbent element includes an absorber body and a packing sheet covering the absorber body,
wherein the packing sheet is formed of laminated nonwoven fabric having a spunbonded layer and a melt-blown layer, and
wherein a moisturizer composed mainly of glycerin is applied to an exterior surface of the top sheet.

Effect of the Invention

As discussed above, the present invention provides advantages in that the skin of a wearer may be protected, leakage of body fluid caused by posture change of the wearer may be avoided, or the like.

BRIEF DESCRIPTION OF THE DRAWINGS

FIG. 1 is a plan view of a tape-type disposable diaper in its spread state, illustrating the inner surface thereof.

FIG. 2 is a plan view of the tape-type disposable diaper in its spread state, illustrating the outer surface thereof.

FIG. 3 is a cross sectional view taken along lines 3-3 in FIG. 1.

FIG. 4 is a cross sectional view taken along lines 4-4 in FIG. 1.

FIG. 5(a) is a cross sectional view taken along lines 5a-5a in FIG. 1, FIG. 5(b) is a cross sectional view taken along lines 5b-5b in FIG. 1, and FIG. 5(c) is a cross sectional view taken along lines 5c-5c in FIG. 1.

FIG. 6 shows enlarged plan views of a relevant part of examples of the pore pattern in the top sheet or cover nonwoven sheet.

FIG. 7 is an enlarged plan view of a relevant part of an example of the pore pattern in the top sheet or cover nonwoven sheet.

FIG. 8 shows cross sectional views of an adhered area of the cover nonwoven sheet.

FIG. 9 illustrates a pore in the cover nonwoven sheet in a perspective view in FIG. 9(a), in a plan view in FIG. 9(b), and in a cross sectional view in FIG. 9(c), taken along lines 1-1 in FIG. 9(b).

FIG. 10 illustrates a pore in the cover nonwoven sheet in a perspective view in FIG. 10(a), in a plan view in FIG. 10(b), and in a cross sectional view in FIG. 10(c), taken along lines 1-1 in FIG. 10(b).

FIG. 11 shows flow diagrams of equipment for bonding a perforated nonwoven fabric.

FIG. 12 is a sectional view of a relevant part, illustrating the perforating step.

FIG. 13 shows sectional views of a relevant part, illustrating the adhesive transfer step.

FIG. 14 is a sectional view of a relevant part, illustrating the adhesive transfer step.

FIG. 15 shows sectional views of a relevant part, illustrating the bonding step.

FIG. 16 is explanatory plan view illustrating positioning of the moisturizer.

EMBODIMENTS FOR CARRYING OUT THE INVENTION

Embodiments of the present invention will now be explained in detail with reference to the attached drawings. In sectional views, a dotted pattern region represent an adhesive as joining means for joining the components on the top side and the underside of the region, and may be formed by, for example, solid, bead, curtain, summit, or spiral application, or pattern coating (transfer of a hot melt adhesive by relief printing) of a hot melt adhesive, or fixed portions of the elastic members may be formed, in place of or in addition to the above, by application of a hot melt adhesive to the external surface of the elastic members with a comb gun or a surewrap. Examples of the hot melt adhesive include, but not limited to, EVA-based, adherent rubber-based (elastomer-based), polyolefin-based, and polyester/polyamide-based adhesives. The joining means for joining components may alternatively be material melt-bonding, such as heat sealing or ultrasonic sealing.

<Example of Tape-Type Disposable Diaper>

FIGS. 1 to 5 show an example of a tape-type disposable diaper as a disposable wearable article according to the present invention, wherein X refers to the overall width of the diaper except for the fastening tapes, and Y refers to the overall length of the diaper. This tape-type disposable diaper has an absorber body 56 extending from the ventral to dorsal sides, a liquid-pervious top sheet 30 covering the top side of the absorber body 56, and a liquid-impervious sheet 11 covering the underside of the absorber body 56, and has a ventral end flap EF and a dorsal end flap EF extending on the front and back sides, respectively, and not including the absorber body 56, and a pair of side flaps SF extending laterally from the opposed side edges of the absorber body 56. Each side flap SF has a narrowed portion in the middle of the front-back direction, which will fit around each leg, and a fastening tape 13 on the dorsal side of the narrowed portion.

The liquid-impervious sheet 11 is covered on its under face with a cover nonwoven sheet 20. The cover nonwoven sheet 20 extends to the peripheries of the diaper, whereas the liquid-impervious sheet 11 extends in the front-back direction up to the front and back edges of the diaper, and in the width direction up to between each side edge of the absorber body 56 and each side edge of the cover nonwoven sheet 20. However, the cover nonwoven sheet 20 may extend partially in the front-back direction, partially in the width direction, or both, as necessary. For example, when part of the liquid-impervious sheet 11 is covered with another material, such as gather nonwoven fabric, the cover nonwoven sheet 20 may not be provided over that part.

The top sheet 30 and the liquid-impervious sheet 11 in the illustrated embodiment are rectangular, and have dimensions slightly larger in the front-back and width directions than those of the absorbent element 50. The peripheral portions of the top sheet 30 extending beyond the side edges of the absorbent element 50 and the peripheral portions of the liquid-impervious sheet 11 extending beyond the side edges of the absorbent element 50 are joined, for example, with a hot melt adhesive.

The absorber body 56 is packed in a packing sheet 58 and may be interposed as the absorbent element 50 between the top sheet 30 and the liquid-impervious sheet 11, while an intermediate sheet 40 may be interposed between the top sheet 30 and the absorbent element 50.

The intermediate sheet 40 in the illustrated embodiment is shorter than the width of the absorbent element 50 and disposed in the center, but may be provided all over the width. The longitudinal dimension of the intermediate sheet 40 may be the same as the overall length of the diaper, the same as the length of the absorbent element 50, or within a small length range around the area where liquids are received. In addition, an indicator may be provided which changes color upon contact with a liquid component of the bodily waste.

On the top face of the tape-type disposable diaper on each side in the width direction, a side gather part 60 is provided. Each side gather part 60 has a first portion 61 provided on the side flap SF (planar gather portion) and a second portion 69 protruding over each side portion of the top sheet 30 (three-dimensional gather portion).

Specifically, a strip of gather nonwoven fabric 62 having the same length as the overall length Y of the diaper extends from the first portion 61 to the second portion 69. In the first portion 61, the gather nonwoven fabric strip 62 is joined to the cover nonwoven sheet 20, for example, with a hot melt adhesive, and between these nonwoven strip and sheet, one or a plurality at intervals in the width direction WD, of gathering elastic members 63 extending in the front-back direction LD are fixed in the extended state and, with the contracting force of the gathering elastic members, the first portion 61 is contracted in the front-back direction LD to form planar gathers, which will be brought into contact around each leg.

The gather nonwoven fabric strip 62 has an extending portion extending from the first portion 61 as the base toward the center of the width direction WD, and at least this extending portion is folded back in the leading edge portion to form a double-layered structure. The ends opposed in the front-back direction LD of the extending portion are fixed to the top sheet 30 to form laid-down portions 67, whereas the middle portion in the front-back direction LD located between the laid-down portions 67 forms a non-fixed, free portion 68. In the free portion 68, one or the plurality at intervals in the width direction WD, of gathering elastic members 63 extending in the front-back direction LD are fixed in the extended state and, with their contracting force, the free portion 68 of the second portion 69 is contracted in the front-back direction LD to form three-dimensional gathers, which will be brought into contact around each leg.

The fastening tape 13 in the illustrated embodiment has a base sheet forming a tape attachment portion 13C fixed to a side portion of the diaper and a tape body 13B protruding from the tape attachment portion 13C, and an engaging part 13A disposed on the tape body 13B of the base sheet in the middle of the width direction and to be engaged on the ventral side, and the portion beyond this engaging part 13A is a grip portion. The tape attachment portion 13C of the fastening tape 13 is interposed between the gather nonwoven fabric 62 as an inner layer and the cover nonwoven sheet 20 as an outer layer of the side flap, and adhered thereto with a hot melt adhesive. The engaging part 13A is joined to the inner surface of the tape body 13B with an adhesive.

The engaging part 13A may preferably be a hook member (male part) of a mechanical fastener (hook and loop fastener). The hook member has a number of engaging projections on its outer surface. The engaging projections may be (A) tick-shaped, (B) J-shaped, (C) mushroom-shaped, (D) T-shaped, (E) double J-shaped (wherein J-shaped parts are joined back to back), or the like, and may be in any of these. Needless to say, the engaging part of the fastening tape 13 may be a sticky material layer.

The base sheet forming from the tape attachment portion 13C to the tape body 13B may be formed of nonwoven fabric, plastic film, polyethylene-laminated nonwoven fabric, paper, or composites thereof.

For fitting the diaper on a wearer, with the dorsal side flaps SF overlapping the exterior of the ventral side flaps SF, the fastening tapes 13 are engaged in the ventral region F on the outer surface at appropriate sites. The position and the size of the sites to be engaged by the fastening tapes 13 may be decided arbitrarily.

At the sites in the ventral region F to be engaged by the fastening tapes 13, a target sheet 24 having targets for facilitating the engagement is preferably disposed. When the engaging part 13A is a hook member, the target sheet 24 may preferably be a film type having a film layer and an engaging layer provided over the outer surface of the film layer, on which engaging layer the hooks of the engaging part 13A detachably engage. In this case, the engaging layer is known to be a thread-knit web having loops, which is to be attached to the film layer, or a nonwoven layer of a thermoplastic resin, which is to be attached to the film layer through intermittent ultrasonic seals so that the fibers of the nonwoven fabric form loops. Either of these may preferably be used. Further, a filmless target tape may also be used, which is formed of embossed nonwoven fabric of a thermoplastic resin and has no film layer. On such a target tape, fastening tapes 13 engage with the hooks thereof being entangled or hooked on the loops.

When the engaging part 13A is a sticky material layer, a base sheet made of plastic film with a sticky smooth surface which has been subjected to release lining, may be used.

When the sites in the ventral region F to be engaged by the fastening tapes 13 are of nonwoven fabric, e.g., when the cover nonwoven sheet 20 in the illustrated embodiment is of nonwoven fabric, and the engaging parts 13A of the fastening tapes 13 are hook members, the target sheet 24 may be omitted, and the hook members may be caught on the nonwoven fabric of the cover nonwoven sheet 20 for engagement. In this case, the target sheet 24 may be interposed between the cover nonwoven sheet 20 and the liquid-impervious sheet 11.

The end flaps EF extend on the front and back sides of the absorbent element 50 and do not include the absorber body 56. Extending on the front side is the ventral end flap EF, and extending on the back side is the dorsal end flap EF.

The front-back dimension of the dorsal end flap EF is preferably the same as or smaller than the front-back dimension of the attachment portion of the fastening tape 13 for the reason mentioned above. If the absorbent element 50 is positioned too close to the dorsal end portion of the diaper, the thickness and stiffness of the absorbent element 50 tend to cause a gap between the dorsal end portion of the diaper and the body surface, so that the front-back dimension of the dorsal end flap EF is preferably 10 mm or larger.

The front-back dimensions of the ventral end flap EF and the dorsal end flap EF are preferably about 5 to 20% the front-back dimension Y of the overall diaper, and in baby diapers, 10 to 60 mm, particularly 20 to 50 mm.

For improved dorsal fitting of the diaper, as shown in detail in FIG. 5, an elastic member which is resiliently stretchable in the width direction, in particular, a strip-shaped dorsal stretchable sheet 70 is preferably provided between the opposed fastening tapes 13. Each end portion of the dorsal stretchable sheet 70 preferably extends to overlap the attachment portion of the corresponding fastening tape 13, but may be spaced apart from the attachment portion toward the center of the width direction. The front-back dimension of the dorsal stretchable sheet 70 is preferably about 20% larger or smaller than the front-back dimension of the attachment portion of the fastening tape 13. Further, when the dorsal stretchable sheet 70 is arranged overlapping the boundary between the dorsal end flap EF and the absorbent element 50 as illustrated, the dorsal end portion of the absorbent element 50 is pressed tightly onto the body, which is preferable.

The dorsal stretchable sheet 70 may be a sheet-shaped elastic member like a rubber sheet but, in view of air permeability, may preferably be nonwoven fabric or paper. In this case, air-permeable sheet-shaped elastic member like stretchable nonwoven fabric may be used but, as shown in FIG. 5(*a*), it is preferred to use two base sheets 71, such as of nonwoven fabric, bonded together with an adhesive, such as a hot melt adhesive, to fix therebetween elastic members 72 in the form of a perforated sheet, web, or elongate (thread, string, or the like) shape, or the like, in the stretched state in the width direction. The base sheet 71 here may be formed of a material similar to the cover nonwoven sheet 20. The elastic members 72 preferably have an elongation of about 150 to 250%. When the elastic members 72 are in an elongate shape (thread, string, or the like), it is preferred to use five to fifteen threads of the elastic members each having a fineness of 420 to 1120 dtex at 3 to 10 mm intervals.

As shown in FIG. 5(*a*), by arranging part of the elastic members 72 across the absorbent element 50, fitting of the absorbent element 50 is preferably improved. In this case, by causing part or all of the elastic members 72 superimposed on the absorbent element 50 to lose their contracting force, e.g., by cutting, the absorbent element 50 is kept from contracting in the width direction in its dorsal end portion, which further improves fitting.

Note that the elastic members 72 may be fixed over the entire length of the base sheets 71 along the longitudinal direction of the sheet (width direction of the diaper) but, for preventing contraction or turning-over of the sheet upon attachment to the diaper body, the contracting force may be caused to be lost or the elastic members 72 may be caused to be absent in the area of about 5 to 20 mm from each end of the sheet in the front-back direction (width direction of the diaper).

The dorsal stretchable sheet 70, in the illustrated embodiment, is interposed between the gather nonwoven fabric 62 and the cover nonwoven sheet 20 on each lateral side of the liquid-impervious sheet 11 in the width direction, and between the liquid-impervious sheet 11 and the absorbent element 50 in the area overlapping the liquid-impervious sheet 11, but may be placed between the liquid-impervious sheet 11 and the cover nonwoven sheet 20, on the exterior surface of the cover nonwoven sheet 20, or between the top sheet 30 and the absorbent element 50.

Further, the dorsal stretchable sheet 70 may be placed on the top sheet 30 and, in this case, on the gather nonwoven fabric 62 on each lateral side of the liquid-impervious sheet 11 in the width direction. When the cover nonwoven sheet 20 is formed by stacking a plurality of base sheets, the entire dorsal stretchable sheet 70 may be interposed between the base sheets of such cover nonwoven sheet 20.

<Basic Structure of the Present Invention>

The disposable wearable article according to the present invention has, referring to the explanatory reference numerals used in the above discussion of the embodiment, a top sheet 30 constituting a surface for use, a liquid-impervious sheet 11 provided on the under face side, and an absorbent element 50 interposed therebetween, wherein the top sheet 30 is formed of perforated nonwoven fabric having a number of holes 14 arranged at intervals and each penetrating two sides of the fabric, wherein the absorbent element 50 includes an absorber body 56 and a packing sheet 58 covering the absorber body 56, wherein the packing sheet 58 is formed of laminated nonwoven fabric having a spunbonded layer and a melt-blown layer, and wherein a moisturizer M composed mainly of glycerin is applied to the exterior surface of the top sheet 58 (see FIG. 16).

According to the basic structure of the present invention, the top sheet 30, which is formed of perforated nonwoven fabric having a number of holes arranged at intervals and each penetrating two sides of the fabric, allows smooth passage of body fluid, particularly loose stool components, through its holes 14 to the absorbent element 50 side, for example, via the intermediate sheet 40 to the absorbent element 50 side.

In this light, the leak protection function against body fluid may be exhibited.

The packing sheet 58 covering the absorber body 56 is of laminated nonwoven fabric (composite nonwoven fabric) having a spunbonded layer and a melt-blown layer, and is composed of, for example, a SMS nonwoven fabric or SMMS nonwoven fabric. Such packing sheet is softer and lower in bending rigidity, compared to the case where the absorber body 56 is covered with tissue, in particular crepe paper.

As a result, the disposable wearable article, when worn, deforms well (flexes well) in response to the posture change of a wearer to ensure contact with the skin of the wearer, which improves the leak protection effect.

Further, the moisturizer M composed mainly of glycerin, which is applied to the exterior surface of the top sheet 30 (containing the moisturizer M at least in the exterior surface portion), has functions not only to protect the skin of a wearer, but also to reduce friction with the skin of a wearer.

As a result, when the disposable wearable article is worn, the top sheet slides with respect to the skin in response to the posture change of a wearer to ensure contact with the skin of the wearer, which improves the leak protection effect.

The top sheet 20 is formed of perforated nonwoven fabric having a number of holes 14. Though the exact reason is not known, a number of holes 14 makes smaller the area in contact with the skin of a wearer compared to nonwoven fabric without holes, to thereby exhibit function to reduce friction with the skin of the wearer.

As a result, when the disposable wearable article is worn, the top sheet slides with respect to the skin in response to the posture change of a wearer to ensure contact with the skin of the wearer, which improves the leak protection effect.

The plan arrangement of the holes 14 in the top sheet 30 may be in a regularly repeated pattern, such as a rhombic lattice pattern as shown in FIG. 6(*a*), a hexagonal lattice pattern as shown in FIG. 6(*b*) (also referred to as a staggered pattern), a square lattice pattern as shown in FIG. 6(*c*), a rectangular lattice pattern as shown in FIG. 6(*d*), a parallelogrammatic lattice pattern as shown in FIG. 6(*e*) (as illustrated, a pattern having two intersecting groups of a number of slanted parallel lines), or the like pattern (including those slanted by less than 90 degrees with respect to the front-back direction LD), as well as a pattern wherein groups of holes 14 (the arrangement in each unit group may be regular or irregular, and may be in a pattern, letter, or the like) are repeated regularly.

The distance 14*y* in the front-back direction and the distance 14*x* in the width direction between adjacent holes 14 in the top sheet may suitably be decided and, in view of air-permeability, preferably 14*y* may be 0.9 to 8.0 mm and 14*x* may be 2.0 to 10 mm, in particular, 14*y* is 1.0 to 3.0 mm and 14*x* is 3.0 to 5.0 mm. In particular, as shown in FIG. 6(*d*), it is preferred that lines of holes 14 arranged in the front-back direction at front-back intervals 14*y* smaller than the front-back dimension 14L of each pore 14 are repeated at predetermined intervals in the width direction WD, with the interval 14*x* in the width direction being larger than the front-back dimension 14L of each pore 14 (more preferably, three times or more the dimension 14W of each pore 14 in the width direction), which leads to significant increase in air permeability without losing softness and bulkiness, and without decrease in tensile strength of the sheet in the front-back direction, which is important during production, and thus is preferred. In this case, it is particularly preferred that the shape of each pore 14 is elongate in the front-back direction LD.

The plan arrangement of the holes 14 in the top sheet 30 (including the cover nonwoven sheet 20, if necessary) is suitably such that imaginary lines 14*q* connecting adjacent holes 14 form a Moroccan pattern D, as typically shown in FIG. 7.

The exact reason why the Moroccan pattern D provides advantages is not clear, but it is assumed to be because the imaginary linking lines R1, R2 formed of groups of holes 14 form a rhombic lattice, and function as starting lines of deformation to facilitate deformation of the top sheet 30 in the front-back and the width directions.

The top sheet 30 is partially joined to the intermediate sheet 40, and no-pore areas Z each surrounded by a group of holes 14 in the Moroccan pattern D remain as non-deforming or hardly-deforming areas, but followability to wearer's posture change is sufficiently secured by the deformation in the area of the imaginary linking lines R1, R2.

Next, explanations will be made on the components of the embodiment.

<Cover Nonwoven Sheet>

The majority of disposable wearable articles, such as disposable diapers and sanitary napkins, are known to have structures in which an air-permeable liquid-impervious sheet is provided on the underside of an absorber body for preventing bleed-through of absorbed liquid while securing air permeability, and this liquid-impervious sheet is covered on its under face with a cover nonwoven sheet for providing fabric-like appearance and texture.

The cover nonwoven sheet 20 in the embodiment, too, is provided for giving fabric-like appearance and texture. The cover nonwoven sheet 20 covers the liquid-impervious sheet 11 on its underside, and constitutes the product external surface in at least part of the region covering the liquid-impervious sheet 11.

In this case, when an air-permeable liquid-impervious sheet is overlaid with a cover nonwoven sheet, the air-permeability is lowered by the presence of the cover nonwoven sheet. One preferred technique for solving this problem is to employ, as a cover nonwoven sheet, perforated nonwoven fabric having a number of holes penetrating the two sides of the fabric.

In the illustrated embodiment, the cover nonwoven sheet 20 is formed of perforated nonwoven fabric having at intervals a number of holes 14 penetrating the two sides of the fabric. The kind of fibers or the processing method in fiber bonding (interlacing) of the cover nonwoven sheet 20 is not particularly limited, and may suitably be similar to those of the exterior sheet. It is preferred to use an air-through nonwoven fabric with a preferred basis weight of 20 to 30 g/m$^2$, and a preferred thickness of 0.3 to 1.0 mm.

The cover nonwoven sheet 20 may be provided, in view of improvement in air permeability, with the holes 14 all over the front-back and the width directions, in case of tape-type disposable diapers.

The plan shape of each pore 14 (opening shape) in the cover nonwoven fabric may suitably be selected, including those shown in FIGS. 6(a) to 6(e).

Each pore in the cover nonwoven fabric may be elongate as shown in FIGS. 6(a) and 6(b), perfect circular as shown in FIGS. 6(c) and 6(e), elliptical as shown in FIG. 6(d), polygonal, such as triangular, rectangular, or rhombic, start shaped, cloud shaped, or any arbitrary shape.

The size of each pore 14 in the cover nonwoven sheet is not particularly limited, and the maximum dimension 14L in the front-back direction LD is preferably 0.3 to 1.8 mm, particularly 0.4 to 1.0 mm, and the maximum dimension 14W in the width direction WD is preferably 0.2 to 1.5 mm, particularly 0.3 to 1.0 mm. When the shape of each pore 14 is longer in one direction (the overall dimension in one direction is longer than the overall dimension in the direction orthogonal to that direction), such as along hole, elliptical, rectangular, or rhombic shape, the maximum longitudinal dimension is preferably 1.2 to 2.5 times the maximum dimension in the direction orthogonal thereto. Further, when the shape of each pore 14 is longer in one direction, the longitudinal direction of the holes 14 is preferably aligned to the front-back direction LD, but may be aligned to the width direction WD or oblique.

The area of each pore 14 and the area ratio of the holes 14 may suitably be decided, and the area may preferably be about 0.1 to 2.7 mm$^2$ (particularly 0.1 to 1.0 mm$^2$) and the area ratio may preferably be about 1.0 to 15.0% (particularly 5.0 to 10.0%).

On the other hand, the plan arrangement of the holes 14 in the cover nonwoven sheet may be in a regularly repeated pattern, such as a rhombic lattice pattern as shown in FIG. 6(a), a hexagonal lattice pattern as shown in FIG. 6(b) (also referred to as staggered pattern), a square lattice pattern as shown in FIG. 6(c), a rectangular lattice pattern as shown in FIG. 6(d), a parallelogrammatic lattice pattern as shown in FIG. 6(e) (as illustrated, pattern having two intersecting groups of a number of slanted parallel lines), or the like pattern (including those slanted by less than 90 degrees with respect to the front-back direction LD), as well as a pattern wherein groups of holes 14 (the arrangement in each unit group may be regular or irregular, and may be in a pattern, letter, or the like) are repeated regularly.

The plan arrangement of the holes 14 may suitably be decided like as shown in FIG. 6, and a regularly repeated plan arrangement is preferred. As discussed above, the plan arrangement is suitably such that imaginary lines 14q connecting adjacent holes 14 form a Moroccan pattern D.

The distance 14y in the front-back direction and the distance 14x in the width direction between adjacent holes 14 may suitably be decided and, in view of air-permeability, preferably 14y may be 0.9 to 8.0 mm and 14x may be 2.0 to 10 mm, in particular, 14y is 1.0 to 3.0 mm and 14x is 3.0 to 5.0 mm. In particular, as shown in FIG. 6(d), it is preferred that lines of holes 14 arranged in the front-back direction at front-back intervals 14y smaller than the front-back dimension 14L of each pore 14 are repeated at predetermined intervals in the width direction WD, with the interval 14x in the width direction being larger than the front-back dimension 14L of each pore 14 (more preferably, three times or more the dimension 14W of each pore 14 in the width direction), which leads to significant increase in air permeability without losing softness and bulkiness, and without decrease in tensile strength of the sheet in the front-back direction, which is important during production, and thus is preferred. In this case, it is particularly preferred that the shape of each pore 14 is elongate in the front-back direction LD.

As shown in FIG. 8, the circumferential portion of each pore 14, for example, forms a reflexed portion 14e which is reflexed over downwards. Examples of the specific shape may include a first embodiment as shown in FIG. 9 wherein the height 14h of reflexing of the reflexed portion 14e is generally uniform, and a second embodiment as shown in FIG. 10 wherein the reflexed portion 14e has opposed portions with the largest height 14i of reflexing and opposed portions orthogonal thereto with the smallest height 14j of reflexing. The reflexed portion 14e preferably continues in the circumferential direction of each pore to form a cylinder, or the reflexed portion 14e of part or all of the holes 14 may be formed only partially in the circumferential direction of each pore 14. The height 14h, 14i, 14j of reflexing (apparent height observed under optical microscope without pressure) is preferably about 0.2 to 1.2 mm and, in the second embodiment, the largest height 14i of reflexing is preferably about 1.1 to 1.4 times the smallest height 14j of reflexing. As may be seen from the second embodiment, the height of reflexing may vary along the circumferential direction of each pore 14.

The holes 14 may be punched holes 14 of which circumferential edge is formed of cut end of fibers, or non-punched holes 14 of which circumferential edge has few cut end of fibers and which are formed by inserting pins into interfiber gaps to expand (higher fiber density on the edge). For example, when a pore 14 which is longer in one direction is formed by insertion of a pin, the fibers around the pore 14 is pushed outwards or in the vertical direction, to form the reflexed portion (burr) 14e, and the height 14i of reflexing of the longitudinally opposed portions of the pore 14 is larger than the height 14j of reflexing of the opposed portions in the direction orthogonal to the longitudinal direction. The circumferential portion of each pore 14 may have a lower fiber density compared to the area therearound, but may preferably have a similar or higher fiber density. Fibers along the edge of each pore 14 may preferably be fused, but may not be fused.

(Fixing of Cover Nonwoven Sheet)

The cover nonwoven sheet 20 may be fixed to the liquid-impervious sheet 11, for example, via a hot melt adhesive 20H. The cover nonwoven sheet 20 may be fixed all over the front-back and the width directions, or may partially be unfixed. For example, in a tape-type disposable diaper, the cover nonwoven sheet 20, with each side in the width direction being unfixed, is hardly affected even when side portions of the absorber body 56 are somewhat contracted under the influence of the side gathers 60, and is hardly rumpled or bent. In this case, the width of the non-fixed portion on each side in the width direction of the cover nonwoven sheet 20 may suitably be decided, and for example, 3 to 10 mm, preferably 5 to 8 mm.

Characteristically, as shown in FIG. 8, the reflexed portions 14e of the cover nonwoven sheet 20 at least in the top end portion form a bonded portion adhered to the liquid-impervious sheet 11 via a hot melt adhesive 20H, and the remaining portions other than the bonded portions are not adhered. With such a bonded structure, the adhered area is small, which does not impair flexibility, while the circumferential portion of the holes 14 may securely be fixed to the liquid-impervious sheet 11. In particular, the reflexed portions 14e support the cover nonwoven sheet 20 like pillars with respect to the liquid-impervious sheet 11, so that the bulkiness is higher and the air permeability is excellent, compared to a non-perforated nonwoven fabric of the same basis weight.

Typical adhered states may include only the top end portion of the reflexed portions 14e being adhered to the liquid-impervious sheet 11 via a hot melt adhesive 20H as shown in FIG. 8(a), the entire reflexed portions 14e being adhered to the liquid-impervious sheet 11 via a hot melt adhesive 20H as shown in FIG. 8(b), or all the outer region of the top end portion rather than the inner region being adhered to the liquid-impervious sheet 11 via hot melt adhesive 20H, with the inner region of the top end portion being non-adhered as shown in FIG. 8(c). It is preferred that the adhesive is not present on the pore 14 inner surface of the reflexed portions 14e and in the areas of the liquid-impervious sheet 11 above the holes 14, but may stick out somehow.

The bonded state of a reflexed portion 14e is not limited to the illustrated state, as long as at least the top end portion is bonded to the liquid-impervious sheet 11 via a hot melt adhesive 20H, and it is sufficient that each pore 14 is in any of the adhered states discussed above in at least part of its circumference. For example, as in the embodiments shown in FIGS. 9 and 10, where a reflexed portion 14e continues in the circumferential direction of the pore 14 to form a cylinder, the top end portion of the cylinder is in the above-mentioned adhered state preferably all along the circumferential direction, but may partially be in other adhered state or non-adhered. When a reflexed portion 14e is formed only partially along the circumferential direction of the pore 14, it is sufficient that the top end portion of that part is in the above-mentioned adhered state. Further, various adhered states may be present among a number of reflexed portions 14e.

The characteristic bonded structure as discussed above may be produced, for example, in equipment illustrated in FIG. 11, using perforated nonwoven fabric 151 as a cover nonwoven sheet 20, and a supporting sheet 160 as a liquid-impervious sheet 11. That is, the equipment for bonding perforated nonwoven fabric includes a pinned roller 100 having on its circumferential surface a number of pins 101 arranged at intervals, a dented roller 110 arranged facing to the pinned roller 100 and having dents 111 for receiving the pins 101, and an adhesive application roller 120 arranged facing to the pinned roller 100 downstream of the site where the pinned roller 100 faces the dented roller 110 in the rotational direction of the pinned roller 100. These rollers 100, 110, 120 are rotationally driven in the directions shown by the arrows, respectively, in the figure so that the dented roller 110 and the adhesive application roller 120 mesh with the pinned roller 100.

In this equipment, first, belt-shaped continuous nonwoven fabric 150 being unrolled from an original fabric roll, not shown, is passed between the pinned roller 100 and the dented roller 110 to pierce the nonwoven fabric 150 with the pins 101, which forms a number of holes 14 through the nonwoven fabric 150 as shown in FIG. 1, each having in its circumferential portion a reflexed portion (burr) 14e reflexed over away from the pinned roller 100, to thereby provide perforated nonwoven fabric 151 (perforating step). The nonwoven fabric 150 to be supplied is preferably unperforated nonwoven fabric, but perforated nonwoven fabric may be supplied to perform the perforating step.

Next, the perforated nonwoven fabric 151 having the holes 14 formed in the perforating step is guided, while pierced with the pins 101, by the rotation of the pinned roller 100 to the adhesive application roller 120, where the hot melt adhesive 20H held on the circumferential surface is transferred to at least the top end portion of the reflexed portions 14e of the perforated nonwoven fabric 151 (adhesive transfer step), as various embodiments are shown in FIG. 13. The sites on the perforated nonwoven fabric 151 to which the adhesive is transferred are preferably only the top end portion of the reflexed portions 14e, but the adhesive may be transferred to the sites including other areas of the reflexed portions 14e to achieve the above-discussed various adhered states.

The equipment for transferring adhesive is not particularly limited and, in the illustrated embodiment, the adhesive application roller 120 has adhesive retainer dents 121 for receiving the pins 101 and at least the top end portion of the reflexed portions 14e arranged therearound. In the adhesive transfer step, a hot melt adhesive 20H is caused to be retained in the adhesive retainer dents 121, and the pins 101 and at least the top end portion of the reflexed portions 14e arranged therearound are inserted into the adhesive retainer dents 121, to thereby cause the hot melt adhesive 20H in the adhesive retainer dents 121 to adhere to at least the top end portion of the reflexed portions 14e of the perforated nonwoven fabric 151. With such an adhesive application roller 120, the hot melt adhesive 20H, while being kept from leaking through the holes 14, may be transferred securely to at least only the top end portion of the reflexed portions 14e of the perforated nonwoven fabric 151. In general, a hot melt adhesive is more excellent in adhesivity to plastic film compared to nonwoven fabric, and thus application of an adhesive on the nonwoven fabric side leads to a higher bonding strength.

The means for causing the hot melt adhesive 20H to be retained in the adhesive retainer dents 121 is not particularly limited. In the example shown in FIG. 11(a), a coating head (die) 122 and a doctor blade 123 are disposed facing to the circumferential surface of the adhesive application roller 120 in this order in the rotational direction and, as shown in FIG. 14, a constant amount of hot melt adhesive 20H is supplied through the coating head 122 onto the circumferential surface of the rotating adhesive application roller 120 continuously in the circumferential direction, and then the hot melt adhesive 20H applied to the areas of the circumferential surface of the adhesive application roller 120 other than the adhesive retainer dents 121 is scraped toward and introduced into the adhesive retainer dents 121 with the doctor blade 123, and the portion of the adhesive not fitting in the adhesive retainer dents 121 is removed. In this way, the hot melt adhesive 20H is retained substantially only in the adhesive retainer dents 121. Note that, as in the embodiment shown in FIGS. 11(a) and 14, with a hot melt adhesive 20H being retained level in the adhesive retainer dents 121, when the clearance between the area on the circumferential surface of the pinned roller 100 without the pins 101 and the area on the circumferential surface of the adhesive application roller 120 without the adhesive retainer dents 121 is not more than the thickness of the area of the perforated nonwoven fabric 151 without the holes 14, the hot melt adhesive is applied not only to the overall reflexed portions 14e, but also widely therearound, as shown in FIG. 13(a). On the other hand, as shown in FIG. 13(b), when this clearance is more than the thickness of the area of the perforated nonwoven fabric 151 without the holes 14 and not more than the thickness of the area of the perforated nonwoven fabric 151 without the reflexed portions 14e, the hot melt adhesive may be applied only to the top end portion of the reflexed portions 14e.

Even when the clearance between the area on the circumferential surface of the pinned roller 100 without the pins 101 and the area on the circumferential surface of the adhesive application roller 120 without the adhesive retainer dents 121 is not more than the thickness of the area of the perforated nonwoven fabric 151 without the holes 14, the hot melt adhesive may be applied only to the top end portion of the reflexed portions 14e by retaining the hot melt adhesive 20H such that the liquid level of the hot melt adhesive 20H in the adhesive retainer dents 121 is lower than the level of the dents discussed above, as shown in FIG. 13(c). The difference between the liquid level of the hot melt adhesive 20H in the adhesive retainer dents 121 and the level of the dents discussed above is not particularly limited as long as the hot melt adhesive 20H is applied only to the top end portion of the reflexed portions 14e, and may preferably be not higher than the height of reflexing of the reflexed portions 14e.

Means for retaining the hot melt adhesive may be apparatus, for example as shown in FIG. 11(b), equipped with a transfer projection roller 125 which has a number of projections to be inserted into the adhesive retainer dents 121 and is positioned facing to the adhesive application roller 120, and a transfer dent roller 124 which has a number of dents for receiving the projections on the transfer projection roller 125 and is positioned facing to the transfer projection roller 125, wherein a coating head (die) 122 and a doctor blade 123 are disposed facing to the circumferential surface of the transfer dent roller 124 in this order in the rotational direction, and these rollers 120, 125, 124 are rotationally driven in the direction shown by the arrows, respectively, in the figure so that the adhesive application roller 120 and the transfer dent roller 124 mesh with the transfer projection roller 125. In the embodiment illustrated in FIG. 11(b), a hot melt adhesive is introduced only into the dents on the rotating transfer dent roller 124, and then the projections on the transfer projection roller 125 are inserted into the dents, so that the hot melt adhesive in the dents on the transfer dent roller 124 is adhered to the projections on the transfer projection roller 125, and then the projections on the transfer projection roller 125 are inserted into the adhesive retainer dents 121 on the adhesive application roller 120, which results in the hot melt adhesive on the projections of the transfer projection roller 125 adhered within the adhesive retainer dents 121 of the adhesive application roller 120. In this way, with the intervention of the transfer dent roller and the transfer projection roller, all of the hot melt adhesive filling level the dents of the transfer dent roller is not supplied to the adhesive retainer dents 121 of the adhesive application roller 120, so that the liquid level of the hot melt adhesive 20H in the adhesive retainer dents 121 of the adhesive application roller 120 is lower than the level of the dents discussed above, and thus the hot melt adhesive 20H may be applied only to the top end portion of the reflexed portions 14e.

As another means for retaining a hot melt adhesive, proposed is a system, not shown, wherein a hot melt adhesive is supplied through the bottom of the adhesive retainer dents 121 of the adhesive application roller 120. In this case, by regulating the amount of the hot melt adhesive to be supplied, the liquid level of the hot melt adhesive 20H in the adhesive retainer dents 121 may freely be adjusted, which allows the hot melt adhesive 20H to be retained at a lower level compared to the above-mentioned level of the dents.

On the other hand, the perforated nonwoven fabric 151 onto which the hot melt adhesive 20H has been transferred, is removed from the pinned roller 100 as it rotates, and then the surface having the hot melt adhesive 20H is overlaid with a supporting sheet 160 and adhered under pressure between pressure rollers 140 (bonding step). Through such techniques, a bonded structure may be produced wherein the reflexed portions 14e of the perforated nonwoven fabric 151 is adhered at least in the top end portion to the supporting sheet 160 via a hot melt adhesive 20H, while the remaining portions other than the adhered portions are not adhered to the supporting sheet 160 via a hot melt adhesive.

<Diversion of Bonded Structure>

In the above embodiment, perforated nonwoven fabric is used as a cover nonwoven sheet 20 covering the underside of the liquid-impervious sheet 11, and the bonded structure between this perforated nonwoven fabric and the liquid-impervious sheet 11 is discussed.

This bonded structure may be applied to a bonded structure between the top sheet 30, which is of perforated nonwoven fabric, and the intermediate sheet 40.

Of course, in bonding the top sheet 30 and the intermediate sheet 40, thermal adhesion or ultrasonic adhesion may be used, but hot melt adhesion is preferred for securing softness.

(Top Sheet)

The top sheet 30 has a property to permeate liquid, and may be formed of, for example, perforated or non-perforated nonwoven fabric or porous plastic sheet. Among these, the nonwoven fabric is not particularly limited in its raw material fibers. For example, synthetic fibers, such as olefin-based including polyethylene or polypropylene, polyester-based, or polyamide-based fibers, recycled fibers, such as rayon or cupra, natural fibers, such as cotton, or mixed fibers or composite fibers of two or more of these may be used. Further, the nonwoven fabric may have been produced through any processing. The processing may include known processes, such as spunlacing, spunbonding, thermal bonding, melt-blowing, needle punching, air through, and point bonding. For example, when flexibility or draping properties are required, spunbonding or spunlacing is preferred, whereas when bulkiness or softness is required, air through, point bonding, or thermal bonding is preferred.

In particular, nonwoven fabric produced by air through method is preferred in view of bulkiness and softness.

The nonwoven fabric fibers may be, for example, of PE/PET of 1.5 to 3.5 dtex.

The basis weight of the top sheet 30 is preferably 10 to 30 g/m$^2$. At less than 10 g/m$^2$, back flow of the body liquid may occur, whereas at over 30 g/m$^2$, sufficient softness may be hard to be obtained.

The top sheet 30 may be made of one sheet, or of a laminated sheet obtained by bonding two or more sheets together. Similarly, the top sheet 30, in the planar direction, may be made of one sheet or of two or more sheets.

The top sheet 30 may be folded around along the side edges of and onto the underside of the absorbent element 50, or may extend beyond the side edges of the absorbent element 50 without being folded.

The top sheet 30 is preferably fixed to the member contiguous on its underside by joining means through material melt-bonding, such as heat sealing or ultrasonic sealing, or with a hot melt adhesive, for the purpose of avoiding displacement with respect to the underside member. In the illustrated embodiment, the top sheet 30 is fixed, with the hot melt adhesive applied on its under face, to the top face of the intermediate sheet 40 and to the surface of an area of the packing sheet 58 located over the top side of the absorber body 56.

(Intermediate Sheet)

For prompt passage of the liquid penetrating the top sheet 30 to the absorber body, an intermediate sheet (also referred to as a second sheet) 40 may be provided, of which liquid permeation rate is faster than that of the top sheet 30. This intermediate sheet 40 is capable not only of promptly passing liquid to the absorber body to increase absorption performance by the absorber body, but also preventing "back flow" phenomenon of the absorbed liquid back from the absorber body to keep the top sheet 30 surface always dry. The intermediate sheet 40 may be omitted.

The intermediate sheet 40 may be formed of the materials similar to those for the top sheet 30, or spunlaced, spunbonded, SMS, or pulp nonwoven fabric, pulp-rayon composite sheets, point-bonded fabric, or crepe paper. In particular, air through nonwoven fabric is preferred for its bulkiness. For air through nonwoven fabric, composite fibers of core-shell structure are preferably used, wherein the resin for the core may be polypropylene (PP), or preferably polyester (PET), which is highly rigid. The basis weight is preferably 20 to 80 g/m$^2$, more preferably 25 to 60 g/m$^2$. The fineness of the raw material fibers of the nonwoven fabric is preferably 2.0 to 10 dtex. For making nonwoven fabric bulky, it is also preferred to use eccentric fibers having off-centered cores, hollow fibers, or eccentric hollow fibers, entirely as the raw material fibers or partially mixed fibers.

In the illustrated embodiment, the width of the intermediate sheet 40 is shorter than the width of the absorber body 56 and the intermediate sheet 40 is arranged in center, but may be provided over the entire width. The longitudinal dimension of the intermediate sheet 40 may be the same as the entire length of the diaper, the same as the length of the absorbent element 50, or within a short length around the liquid receiving area.

The intermediate sheet 40 is preferably fixed to the member contiguous on its underside by joining means through material melt-bonding, such as heat sealing or ultrasonic sealing, or with a hot melt adhesive, for the purpose of avoiding displacement with respect to the underside member. In the illustrated embodiment, the intermediate sheet 40 is fixed, with the hot melt adhesive applied on its under face, to the surface of that area of the packing sheet 58 which is located over the top side of the absorber body 56.

(Liquid Impervious Sheet)

Materials of the liquid-impervious sheet 11 is not particularly limited, and may be, for example, plastic film made of polyolefin-based resins or the like, such as polyethylene or polypropylene, laminated nonwoven fabric wherein plastic film is laminated over nonwoven fabric, or a laminated sheet wherein nonwoven fabric or the like is laid over and joined on plastic film. The liquid-impervious sheet 11 may be made of a material which is preferably used for preventing dampness and is not liquid-pervious and is moisture-permeable. As moisture-permeable plastic film, microporous plastic film is widely used, which is obtained by kneading an inorganic filler in a polyolefin-based resin, such as polyethylene or polypropylene, molding the resulting mixture into a sheet, and then uni- or biaxially drawing the sheet. Also, nonwoven fabric of microdenier fibers, or sheets that have been rendered liquid-impervious without using plastic film through a process, such as enhancement of leak proof property by applying heat or pressure to minimize interfiber gaps, or coating with a highly water-absorbable resin or a hydrophobic resin or water repellent, may be used as the liquid-impervious sheet 11. For sufficient bonding strength in bonding to a cover nonwoven sheet 20 via a hot melt adhesive as will be discussed later, use of plastic film is preferred.

The liquid-impervious sheet 11 may have a width to fit behind the absorbent element 50 as illustrated, or may be folded around both side edges of the absorbent element 50 to extend to the opposed sides of the top sheet 30. The width of such extensions may suitably be about 5 to 20 mm on each opposed side.

Inside of the liquid-impervious sheet 11, in particular on the side faces of the absorber body 56, an excretion indicator which changes in color upon absorption of a liquid component, may be provided.

(Side Gather Part)

Each side gather part 60 extends all over the front-back direction LD, and is provided to be brought into contact around each leg of a wearer to prevent side leakage. Those generally referred to as three-dimensional gathers 69 and planar gathers 61 fall under this part.

The gather nonwoven fabric 62 may preferably be flexible nonwoven fabric having excellent uniformity and concealability, such as spunbonded nonwoven fabric (SS, SSS, or the like), SMS nonwoven fabric (SMS, SSMMS, or the like), or melt-blown nonwoven fabric, which may have been subjected to water-repellent treatment with silicone or the like, as required. The basis weight of the fibers may preferably be about 10 to 30 g/m$^2$. The elongate elastic members 63 may be of rubber thread or the like. When spandex rubber thread is used, the fineness is preferably 470 to 1240 dtex, more preferably 620 to 940 dtex. The stretch rate in the fixed state is preferably 150 to 350%, more preferably 200 to 300%. Note that the term "stretch rate" refers to a value with respect to the natural length being 100%. Further, as illustrated, a waterproof film may be interposed between duplicate gather nonwoven fabric 62. In this case, the gather nonwoven fabric 62 may partially be omitted in the area where the waterproof film is present, but in order to impart fabric-like appearance and texture to the product, the exterior of each side gather part 60 at least from its root end to its leading edge is required to be formed of the gather nonwoven fabric 62, as in the illustrated embodiment.

The number of the elongate elastic members 63 provided in the free section of each side gather part 60 is preferably 2 to 6, more preferably 3 to 5.

(Absorbent Element)

The absorbent element 50 includes the absorber body 56 and the packing sheet 58 packing the entire absorber body 56.

(Absorber Body)

The absorber body 56 may be formed of an assembly of fibers. Such an assembly of fibers may be an accumulation of short fibers of fluff pulp, synthetic fibers, or the like, as well as an assembly of filaments obtained by opening, where necessary, a tow (fiber bundle) of synthetic fibers, such as cellulose acetate. The basis weight of the fibers may be about 100 to 300 $g/m^2$ for an accumulation of fluff pulp or short fibers, and about 30 to 120 $g/m^2$ for an assembly of filaments. The fineness of the synthetic fibers, when used, is, for example, 1 to 16 dtex, preferably 1 to 10 dtex, more preferably 1 to 5 dtex. In an assembly of filaments, the filaments may be formed of uncrimped fibers, but crimped fibers are preferred. The number of crimps of the crimped fibers may be, for example, 5 to 75, preferably 10 to 50, more preferably 15 to 50 per inch. Uniformly crimped fibers are often used. In the absorber body 56, superabsorbent polymer particles are preferably dispersed and retained.

The absorber body 56 may be in a rectangular shape, or in the shape of an hourglass having the front end, the back end, and a narrowed section located between the front and back ends and having a narrower width compared to the front and back ends.

The size of the absorber body 56 may suitably be decided as long as the absorber body extends to the front, back, left, and right of the position of the urination port.

(Superabsorbent Polymer Particles)

The absorber body 56 may be caused partially or entirely to contain superabsorbent polymer particles. The superabsorbent polymer particles include not only "particles", but also "powders". The superabsorbent polymer particles may be those used in this type of disposable diapers as they are, and may preferably be particles 30 wt % or less of which, after sieving (five-minute shaking), remain on a 500 μm standard sieve (JIS Z8801-1: 2006) and particles 60 wt % or more of which, after sieving (five-minute shaking), remain on a 180 μm standard sieve (JIS Z8801-1: 2006).

Any material of the superabsorbent polymer particles may be used without particular limitation, and those having a water absorption of 40 g/g or more are preferred. The superabsorbent polymer particles may be formed of starch-based, cellulose-based, or synthetic polymer-based. Starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption rate of 70 seconds or less, particularly 40 seconds or less, may preferably be used. With too slow a water absorption rate, so-called back flow may likely to occur, wherein liquid supplied into the absorber body 56 returns out of the absorber body 56.

The superabsorbent polymer particles may preferably be those having a gel strength of 1000 Pa or higher. With such property, when the superabsorbent polymer particles are formed into a bulky absorber body 56, stickiness after liquid absorption may effectively be limited.

The basis weight of the superabsorbent polymer particles may suitably be decided depending on the absorption amount required in a use of the absorber body 56. Thus, it depends, but the basis weight may be 50 to 350 $g/m^2$. At a basis weight of the polymer less than 50 $g/m^2$, the absorption amount may hardly be secured. At over 350 $g/m^2$, the effect may be saturated.

Where necessary, the spread density or spread amount of the superabsorbent polymer particles may be adjusted in the horizontal direction of the absorber body 56. For example, the spread amount on the liquid excretion area may be larger than that on the remaining areas. Considering the sexual difference, the spread density (amount) on the front side may be higher for men's, whereas the spread density (amount) in the center portion may be higher for women's. Further, the absorber body 56 in its horizontal direction may be provided with a local (e.g., spot) area without the polymer.

(Packing Sheet)

For limiting escape of the superabsorbent polymer particles, or for improving maintenance of the shape of the absorber body 56, the absorber body 56 is wrapped with a packing sheet 58.

The material of the packing sheet 58, when used, may be tissues, in particular, crepe paper, nonwoven fabric, polyethylene-laminated nonwoven fabric, perforated sheet, or the like.

Conventionally, crepe paper is often used. In the present invention, SMS nonwoven fabric (spunbonded/melt-blown/spunbonded laminated nonwoven fabric) or SMMS nonwoven fabric (spunbonded/melt-blown/melt-blown/spunbonded laminated nonwoven fabric) is used.

With crepe paper, in which pulp fibers extend in the front-back direction (MD) and arranged densely, rigidity particularly in the front-back direction is high (with less softness).

In contrast, with SMS or SMMS nonwoven fabric, for example, rigidity particularly in the front-back direction is low (with excellent softness), and bending rigidity in the front-back direction (MD) and in the 45-degree oblique direction is lower, compared to those with crepe paper, as will be shown by the results of cantilever test.

As a result, the disposable wearable article, when worn, deforms well (bends well) in response to the posture change of the wearer and is securely brought into contact with the skin of the wearer, which leads to improved leak protection.

The laminated nonwoven fabric having a spunbonded layer and a melt-blown layer may be made from polypropylene, polyethylene/polypropylene composite material, or the like. In particular, nonwoven fabric subjected to hydrophilization treatment for improving body fluid absorption characteristics is preferred.

The laminated nonwoven fabric having a basis weight of preferably 5 to 40 $g/m^2$, particularly 10 to 30 $g/m^2$ is preferred.

How to pack with the packing sheet 58 may suitably be decided and, in view of readiness of production or protection against leakage of the superabsorbent polymer particles through the front or back end edge, preferably the packing sheet 58 is wrapped cylindrically around the absorber body 56 to surround its top and under faces as well as both side faces, with the front and back edge portions of the packing sheet extending forwardly and backwardly beyond the absorber body 56, and the overlaid wrapping portion as well as the overlapped portions in the front and back extensions are joined with joining means, such as a hot melt adhesive or material melt-bonding.

Where needed, the absorber body 56 may be covered only on its top and under faces with two separate sheets of nonwoven fabric, with both side faces being uncovered.

(Moisturizer)

The moisturizer composed mainly of glycerin according to the present invention contains, as its component, 70 mass % or more glycerin and optionally one or a plurality of additives selected from the group consisting of emulsifiers, phosphates, paraffin, and surfactants. The surfactants may preferably be ether-type nonionic surfactants or nonionic surfactants including EO/PO surfactants.

The moisturizer M may be applied to the top sheet 30 over its entire surface, but preferably in a striped pattern extending in the front-back direction at intervals in the width direction of the absorbent article, where the top sheet and the intermediate sheet are bonded together with a hot melt adhesive in a striped or spiral pattern.

Otherwise, as permeation of body fluid occurs mainly in the crotch region, the moisturizer is suitably applied to the crotch region all over or in a striped pattern, as shown in FIG. 16. Note that FIG. 16 shows the positional relationship between the moisturizer and the absorber body 56, not the application position of the moisturizer M on the top sheet 30.

The application amount of the moisturizer M is preferably 0.02 g/m$^2$ or more, more preferably 0.05 g/m$^2$ or more, and preferably 3.00 g/m$^2$ or less, more preferably 1.50 g/m$^2$ or less, specifically 0.05 g/m$^2$ or more and 1.20 g/m$^2$ or less.

<Explanation of Terms in the Specification>

The following terms appearing in the present specification shall have the following meaning unless otherwise specified herein.

The "front-back (longitudinal) direction" refers to the direction connecting the ventral side (front side) and the dorsal side (back side), whereas the "width direction" refers to the direction orthogonal to the front-back direction (right-left direction).

The "top side" refers to the side of a tape-type disposable diaper, when worn, closer to the skin of the wearer, whereas the "underside" refers to the side of a tape-type disposable diaper, when worn, away from the skin of the wearer.

The "top face" refers to the face of a tape-type disposable diaper, when worn, closer to the skin of the wearer, whereas the "under face" refers to the face of a tape-type disposable diaper, when worn, away from the skin of the wearer.

The "area ratio" refers to the ratio of the objective area per unit area, and is represented in percentage by dividing the sum of the areas of objective portions (e.g., holes) in an objective region (e.g., cover nonwoven sheet) by the area of that objective region. In a configuration where a number of objective portions are provided at intervals, the area ratio is preferably determined with the objective region being set to a size containing 10 or more objective portions. For example, the area ratio of the holes may be determined in the following procedure, using, for example, VHX-1000 (tradename) manufactured by KEYENCE under the measurement conditions in ×200 magnification.

(1) Place a specimen under a ×20 magnification lens, and adjust the focus. Position the nonwoven fabric so that 4×6 holes are in the field.

(2) Specify the brightness of the pore portions, and measure the area of the holes.

(3) Click the color extraction in "Area Measurement" under "Measurement and Comment". Click the pore portions.

(4) Click "Collective Measurement", check "Display the measurement result window", and store in CSV data.

The "stretch rate" refers to a value with respect to the natural length being 100%.

The "gel strength" is determined as follows. To 49.0 g of artificial urine (a mixture of 2 wt % urea, 0.8 wt % sodium chloride, 0.03 wt % calcium chloride dihydrate, 0.08 wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curdmeter-MAX ME-500 manufactured by I. techno Engineering).

The "basis weight" is determined as follows. A specimen or test piece is preliminarily dried, left in a laboratory or in apparatus under the standard conditions (20±5° C. temperature and 65% or lower relative humidity in the testing location) until constant mass is attained. The preliminary drying means attaining constant mass from a specimen or test piece in the environment not exceeding a relative humidity of 10 to 25% and a temperature of 50° C. No preliminary drying may be performed on fibers with an official regain of 0.0%. From the test piece of the constant mass, a specimen of 200 mm×250 mm size (±2 mm) is cut out, using a plate of 1 g/m$^2$ (200 mm×250 mm, ±2 mm). The weight of the specimen is measured and multiplied by 20 times to calculate the weight per 1 m$^2$, which is taken as the basis weight.

The "thickness" is automatically measured using an automatic thickness meter (KES-G5 handy compression tester program) under a load of 10 gf/cm$^2$ with the compression area of 2 cm$^2$.

The water absorption is determined in accordance with JIS K7223—1996 "Testing method for water absorption capacity of super absorbent polymers".

The water absorption rate is defined as the "time spent until the end point is reached" in carrying out JIS K7224—1996 "Testing method for water absorption rate of super absorbent polymers" using 2 g of superabsorbent polymer and 50 g of saline.

The "spread state" refers to the state in which an article is spread flatly without contraction or slack.

The size of each part refers to the size not in the natural length state but in the spread state, unless otherwise specified.

Unless the environmental conditions of a test or measurement are otherwise specified, the test or measurement shall be conducted in a laboratory or in apparatus under the standard conditions (20±5° C. temperature and 65% or lower relative humidity in the testing location).

Next, Examples and Comparative Examples are disclosed to demonstrate the effects of the present invention.

<Frictional Force Test>

In the tape-type disposable diaper as shown in FIGS. 1 to 5, the joined sheet in which the top sheet and the intermediate sheet were joined with a hot melt adhesive (applied in a curtain pattern in the amount of 1.1 g/m$^2$) was subjected to measurement of the friction force MIU using a friction tester in accordance with KES. The results are shown in Table 1. The measured value is an average from five measurements.

The holes in staggered pattern are arranged in the pattern as shown in FIG. 6(e). The Moroccan pattern is as shown in FIG. 7.

Here, the top sheet is of 20 g/m² PE-PET air-through nonwoven fabric with the upper layer being 2.0 dtex PE and the lower layer being 2.2 dtex PET.

The intermediate sheet is of 18 g/m² PE-PET air-through nonwoven fabric with the upper layer being 2.2 dtex PE and the lower layer being 4.4 dtex PET.

TABLE 1

|  | MD | CD |
|---|---|---|
| Top sheet without holes | 0.688 | 0.903 |
| Top sheet with holes in staggered pattern | 0.683 | 0.869 |
| Top sheet with holes in Moroccan pattern | 0.647 | 0.811 |
| Top sheet with holes in staggered pattern + moisturizer | 0.663 | 0.873 |
| Top sheet with holes in Moroccan pattern + moisturizer | 0.616 | 0.806 |

Taking note of the results, it is seen that the frictional force was reduced due to the presence of the holes in the top sheet, and among the various top sheets, the one with the holes in the Moroccan pattern resulted in a lower frictional force compared to the one with the holes in the staggered pattern.

Application of the moisturizer, in combination with the Moroccan pattern, resulted in a significantly lower frictional force, through the reason is not known.

<Cantilever Test>

A bonded sheet in which the top sheet and the packing sheet to be used in the tape-type disposable diaper as shown in FIGS. 1 to 5 were bonded with a hot melt adhesive (applied in a curtain pattern in the amount of 7 g/m²) was subjected to a cantilever test at an angle of 45° in accordance with the testing method provided in JIS L 1913: 2010.

As the top sheet, three kinds of top sheets were provided, one with no holes, one with the holes in the staggered pattern, and one with the holes in the Moroccan pattern. These are the same as those subjected to the frictional force test discussed above. As the packing sheet, two kinds of packing sheets were provided, one made of crepe paper (15 g/m²) and one with nonwoven fabric. The nonwoven fabric was SMS nonwoven fabric.

Here, the test was conducted in the orientation that the top sheet, when bent, faced inwards (opposing) with respect to the jig for the cantilever test.

The results are shown in Table 2. The measured value is an average from five measurements. The unit is mm.

TABLE 2

|  | MD | CD | Oblique |
|---|---|---|---|
| Top sheet without holes + crepe paper | 67.4 | 48.0 | 49.2 |
| Top sheet with holes in staggered pattern + crepe paper | 71.0 | 40.2 | 43.8 |
| Top sheet with holes in Moroccan pattern + crepe paper | 76.4 | 40.2 | 58.8 |
| Top sheet with holes in staggered pattern + SMS nonwoven fabric | 60.6 | 31.4 | 41.8 |
| Top sheet with holes in Moroccan pattern + SMS nonwoven fabric | 66.8 | 37.6 | 44.0 |

Taking note of the results, it is seen that with the packing sheet being a laminated nonwoven fabric including a spunbonded layer and a melt-blown layer, for example, SMS nonwoven fabric, the softness was higher and the bending rigidity was lower, compared the case wherein the absorber body was covered with crepe paper.

Note that the bending rigidity of the sheet with the Moroccan pattern showed a bit higher bending rigidity compared to the sheet with the staggered pattern, which is regarded as preferred in view of the overall tendency to closely fit the skin of a wearer.

INDUSTRIAL APPLICABILITY

The present invention may be applied to disposable wearable articles in general, including not only tape-type disposable diapers, but also pad-type disposable diapers, disposable swim wears, diaper covers, sanitary napkins, or the like.

DESCRIPTION OF REFERENCE NUMERALS 11 liquid-impervious sheet
20 cover nonwoven sheet
20H hot melt adhesive
14 hole
30 top sheet
40 intermediate sheet
50 absorbent element
56 absorber body
58 packing sheet
60 side gather part
62 gather nonwoven fabric
LD front-back direction
WD width direction

The invention claimed is:

1. A disposable wearable article comprising a top sheet constituting a surface for use, a liquid-impervious sheet provided on an under face side, and an absorbent element interposed therebetween,
   wherein the top sheet is formed of perforated nonwoven fabric having a number of holes arranged at intervals and each penetrating two sides of the fabric,
   wherein the absorbent element includes an absorber body and a packing sheet covering the absorber body,
   wherein the packing sheet is formed of laminated nonwoven fabric having a spunbonded layer and a melt-blown layer, and
   wherein a moisturizer composed mainly of glycerin is applied to an exterior surface of the top sheet.

2. The disposable wearable article according to claim 1, wherein imaginary lines connecting adjacent holes in the top sheet form a Moroccan pattern.

3. The disposable wearable article according to claim 1, wherein a basis weight of the top sheet is 10 to 30 g/m².

4. The disposable wearable article according to claim 1, wherein a basis weight of the packing sheet is 5 to 40 g/m².

5. The disposable wearable article according to claim 1, wherein the liquid-impervious sheet is covered on its under face side with a cover nonwoven sheet, and the cover nonwoven sheet is formed of perforated nonwoven fabric having a number of holes arranged at intervals and each penetrating two sides of the fabric.

6. The disposable wearable article according to claim 5, wherein imaginary lines connecting adjacent holes in the cover nonwoven sheet form a Moroccan pattern.

* * * * *